(12) United States Patent
Ma et al.

(10) Patent No.: US 12,397,052 B2
(45) Date of Patent: Aug. 26, 2025

(54) MICROCAPSULE-BASED VACCINE

(71) Applicant: INSTITUTE OF PROCESS ENGINEERING, CHINESE ACADEMY OF SCIENCES, Beijing (CN)

(72) Inventors: Guanghui Ma, Beijing (CN); Wei Wei, Beijing (CN); Xiaobo Xi, Beijing (CN); Tong Ye, Beijing (CN); Xiangming Na, Beijing (CN); Shuang Qing, Beijing (CN)

(73) Assignee: INSTITUTE OF PROCESS ENGINEERING, CHINESE ACADEMY OF SCIENCES, Beijing (CN)

( * ) Notice: Subject to any disclaimer, the term of this patent is extended or adjusted under 35 U.S.C. 154(b) by 874 days.

(21) Appl. No.: 17/269,912

(22) PCT Filed: Aug. 16, 2019

(86) PCT No.: PCT/CN2019/101078
§ 371 (c)(1),
(2) Date: Feb. 19, 2021

(87) PCT Pub. No.: WO2020/038298
PCT Pub. Date: Feb. 27, 2020

(65) Prior Publication Data
US 2021/0308258 A1  Oct. 7, 2021

(30) Foreign Application Priority Data
Aug. 20, 2018 (CN) .......................... 201810946808.7

(51) Int. Cl.
| | | |
|---|---|---|
| *A61K 39/29* | (2006.01) | |
| *A61K 9/50* | (2006.01) | |
| *A61K 39/00* | (2006.01) | |
| *A61K 39/39* | (2006.01) | |
| *A61P 35/00* | (2006.01) | |

(52) U.S. Cl.
CPC ............ *A61K 39/29* (2013.01); *A61K 9/5031* (2013.01); *A61K 39/0011* (2013.01); *A61K 39/00117* (2018.08); *A61K 39/39* (2013.01); *A61P 35/00* (2018.01); *A61K 2039/55561* (2013.01); *A61K 2039/55572* (2013.01); *A61K 2039/6093* (2013.01)

(58) Field of Classification Search
CPC .............. A61K 9/5031; A61K 39/0011; A61K 2039/55561
See application file for complete search history.

(56) References Cited

U.S. PATENT DOCUMENTS

| | | | | |
|---|---|---|---|---|
| 6,541,033 B1* | 4/2003 | Shah | ...................... | A61K 47/34 514/909 |
| 2008/0131466 A1* | 6/2008 | Reed | ...................... | A61K 39/35 424/282.1 |
| 2010/0247663 A1* | 9/2010 | Day | ...................... | A61K 9/1682 424/130.1 |
| 2015/0165020 A1* | 6/2015 | Jaklenec | ................. | A61P 31/04 424/234.1 |
| 2016/0263232 A1* | 9/2016 | Amighi | ................ | A61K 31/495 |

FOREIGN PATENT DOCUMENTS

| | | |
|---|---|---|
| CN | 1200732 C | 5/2005 |
| CN | 101461786 A | 6/2009 |
| CN | 101601860 A | 12/2009 |
| CN | 102489230 A | 6/2012 |
| CN | 105194662 A | 12/2015 |
| EP | 2642984 B1 | 1/2017 |
| WO | 2009075652 A1 | 6/2009 |
| WO | 2013082535 A2 | 6/2013 |

OTHER PUBLICATIONS

First Office Action in corresponding Chinese Application No. 201910756019.1, May 28, 2021; 23 pgs.
Second Office Action in corresponding Chinese Application No. 201910756019.1, Oct. 20, 2021; 23 pgs.
Mazzara, J., "Self-Encapsulation of Vaccine Antigens in PLGA Microparticles and Microneedles", University of Michigan 2016 PhD Thesis, Dec. 31, 2016; 187 pgs.
Na, X. et al., "Biodegradable Microcapsules Prepared by Self-Healing of Porous Microspheres", ACS Macro Letters, May 21, 2012; 4 pgs.
Liu, Y. et al., "Surface Hydrophobicity of Microparticles Modulates Adjuvanticity", Journal of Materials Chemistry B, Jun. 19, 2013; 10 pgs.
First Office Action in European Patent Application No. 19851585.0; mailed Dec. 9, 2024; 5 pgs.
International Search Report issued in PCT/CN2019/101078; mailed Dec. 2, 2019; 8 pgs.
Notice of Reasons for Refusal issued in Japanese Patent Application No. 2021-509850; mailed Feb. 1, 2022; 4 pgs.
Terry, Treniece La'Shay; "Ternary Particles for Effective Vaccine Delivery To the Pulmonary System"; Univ. of Iowa, US, Dec. 1, 2008; 24 pgs.

\* cited by examiner

*Primary Examiner* — Andrew S Rosenthal
(74) *Attorney, Agent, or Firm* — HAUPTMAN HAM, LLP

(57) ABSTRACT

A vaccine comprising antigen and a matrix of biodegradable polymer blend, wherein the polymer blend comprises hydrophobic polymer and amphiphilic block copolymer, and the vaccine exists in form of microcapsules that comprise a multi-cavity structure inside, and has an average particle diameter of preferably 10-100 μm and more preferably 30-60 μm, and is prepared by means of the following method: making porous microspheres from the polymer blend, then mixing the porous microspheres with antigen-containing solution, and then sealing openings of porous microspheres that have been loaded with the antigen-containing solution to form an opening-sealed microcapsule loaded with the antigen.

12 Claims, 8 Drawing Sheets

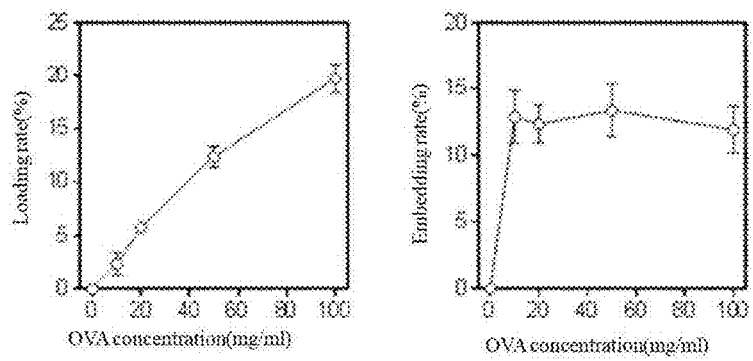
Fig. 9
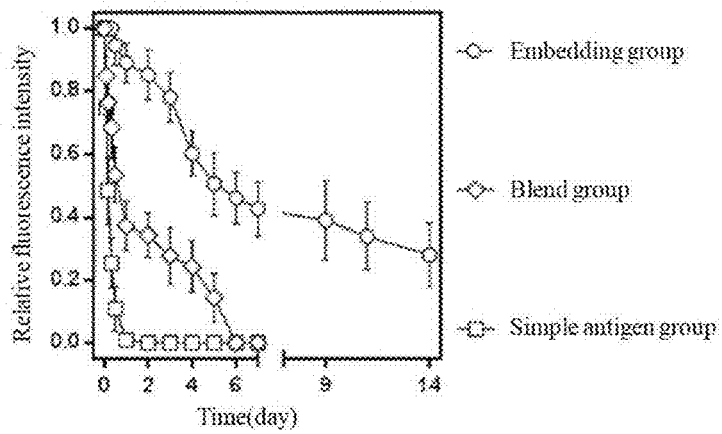
Fig. 10
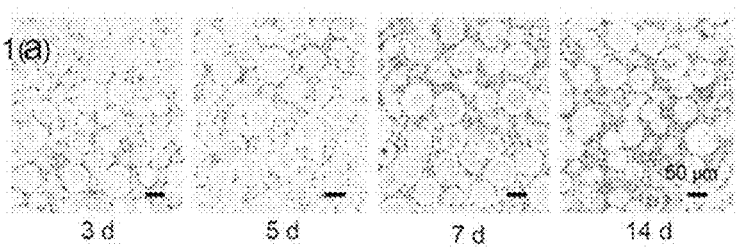
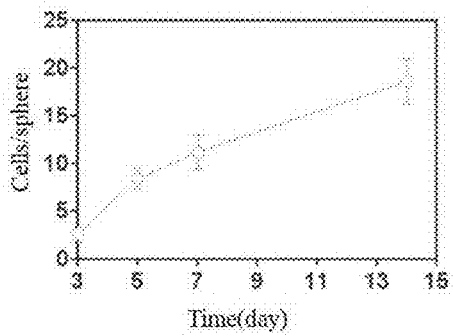

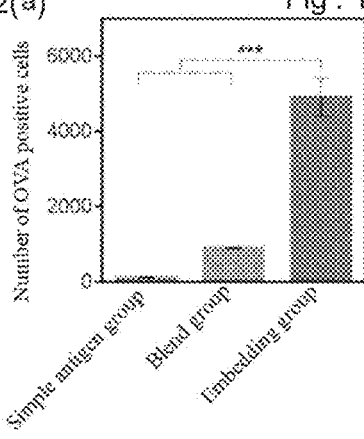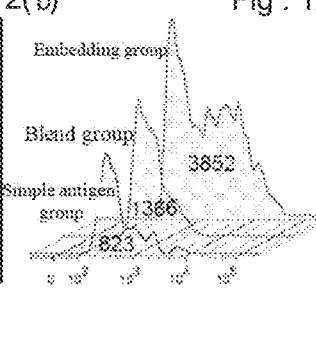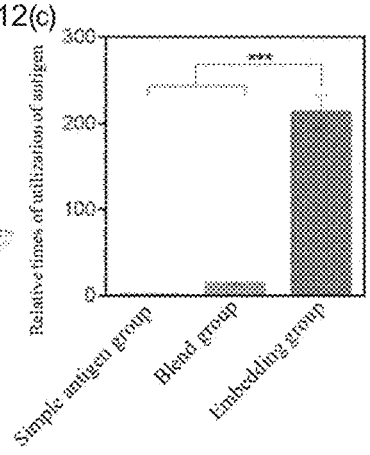
Fig. 12(a)  Fig. 12(b)  Fig. 12(c)
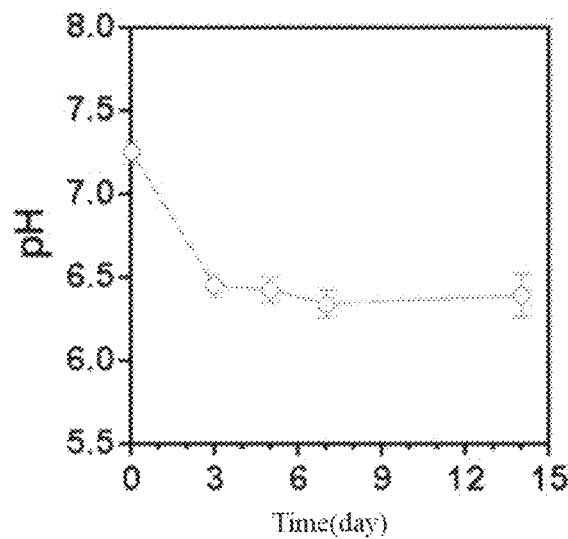
Fig. 13
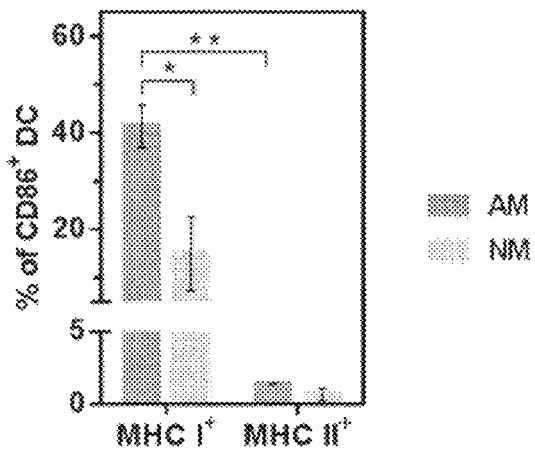
Fig. 14

MICROCAPSULE-BASED VACCINE

RELATED APPLICATIONS

The present application is a National Phase of International Application Number PCT/CN2019/101078 filed Aug. 16, 2019 and claims priority to Chinese Application Number 201810946808.7 filed Aug. 20, 2018.

TECHNICAL FIELD

The disclosure relates to a microcapsule-based vaccine comprising an antigen and a matrix of a biodegradable polymer blend, wherein the vaccine may be, for example, an antitumor vaccine.

BACKGROUND ART

With the development of tumor biology and immunology, immunotherapy, mainly characterized by regulating the autoimmune system, has provided tumor treatment with a brand new idea. Of the many immunotherapeutic strategies, tumor vaccines have received more and more attention because they mimic the way the body fights pathogens and restores the body's natural "recognition" of and response to tumor cells, thereby specifically destroying tumor cells.

One of the difficulties that tumor vaccines are confronted with in acting effectively is that it is difficult for a pure tumor antigen to stimulate a durable and effective immune response in the body. Loading a nano-sized carrier with tumor antigens can effectively improve the endocytosis and maturation of immune cells, thereby stimulating a stronger immune response in the body, however, because of their small size, nano-carriers are prone to be scavenged by the body, making it difficult to produce a durable antitumor effect. Preparing micron-sized carriers by embedding antigens using a double emulsion method effectively circumvents the problem described above, but it faces the dilemma that antigen release is too slow to trigger an effective immune response.

CN101601860A discloses a vaccine based on polymer particles. In the vaccine, the antigen is composed of two forms of antigen, one of which is an antigen adsorbed on biodegradable polymer particles and the other is an antigen not adsorbed (free antigen). The particles have average diameter of 0.1-20 μm. The vaccine is prepared by mixing polymer particles with solution of hepatitis B surface antigen to prepare a polymer particle suspension with effective adsorption of the antigen solution. The vaccine rapidly induced a host immune response, and induced humoral and cellular immunity at a high level in the body.

CN102489230A discloses a method for preparing a microcapsule of biodegradable material. The method comprises preparing porous microspheres, loading the microspheres with a filling material, and sealing the openings of the microspheres. Compared with the traditional double emulsion methods, the method is advantageous in the following aspects: it is milder and can prevent the biologically active substances from being destroyed; the filling material left over in the solution after the loading step can be recycled, so the method is more environmentally friendly; the sizes of the particle and opening reach the same level as previously reported; and the internal cavity has a large volume, which is conducive to the loading of the filling material. However, this patent document only mentions that the biodegradable microcapsule can be used for embedding small molecules and biological macromolecules, and can be loaded with nano- and micron-sized particles.

Despite the studies mentioned above, research and development of vaccines that can better induce specific immunity in the body (such as killing tumor cells by cytotoxic T cells) is of great significance for their clinical application.

SUMMARY OF THE DISCLOSURE

The inventors of the disclosure prepared an opening-sealed microcapsule with a large particle size that could be locally retained in the body of mice, by preparing a porous microsphere made of biodegradable polymers through double emulsion-solvent removal method, filling the porous microsphere with tumor antigen, and finally sealing the openings of the microsphere. The inventors discovered that since the microcapsule hardly be phagocytized or metabolized, could degrade in a certain time period, and during the degradation, activated a continuous inflammatory response in the body, it acted as an antigen depot and continuously recruited antigen-presenting cells (e.g., dendritic cells (DCs)) to the injection site for antigen processing. Besides, with the assistance of the acidic microenvironment produced by the degradation of the polymeric matrix, the microcapsule significantly increased the number of the recruited cells, improved the cells' endocytosis of antigen, induced the maturation and differentiation of DCs—which eventually went back to the lymph node, activated an effective and durable immune response, promoted the continuous proliferation and differentiation of T cells—which produced specific and durable killing effect, and consequently inhibited tumor growth and prolonged the survival of mice.

Based on these discoveries, the disclosure provides a vaccine comprising an antigen and a matrix of a biodegradable polymer blend, wherein the polymer blend comprises a hydrophobic polymer and an amphiphilic block copolymer. The vaccine exists an inform of microcapsule that comprises a multi-cavity structure inside, which has an average particle diameter of preferably 10-100 μm, more preferably 30-60 μm. The microcapsule is prepared by making a porous microsphere from the polymer blend, mixing the porous microsphere with an antigen-containing solution, and sealing openings of the porous microsphere that has been loaded with the antigen-containing solution to form an opening-sealed microcapsule loading with the antigen.

Preferably, by optimizing parameters during the preparation of vaccine, the vaccine creates synergy between the release of antigen and the recruitment of cells when the vaccine is locally retained in the body, which causes that the released antigen to be maximumly phagocytized by the recruited immature DCs, thereby significantly improving the utilization of the antigen.

Preferably, the vaccine is a therapeutic vaccine, such as an antitumor vaccine or a therapeutic hepatitis B vaccine. The antigen is preferably a tumor antigen or a hepatitis B surface antigen.

In the vaccine of the disclosure, the porous microspheres can be loaded with a chemokine such as granulocyte-macrophage colony-stimulating factor (GM-CSF), macrophage inflammatory protein-3α (MIP-3α), and monocyte chemotactic protein-1 (MCP-1) in a certain amount so as to enhance their recruitment of the cells and further improve the utilization of the antigen and the immune response.

DESCRIPTION OF DRAWINGS

FIG. 9 shows the loading rate and embedding rate of the polypeptide MUC1 in the opening-sealed microcapsule according to the disclosure.

FIG. 10 is a quantitative diagram of antigen fluorescence intensity between different vaccine preparations at the injection site.

FIG. 11($a$) and FIG. 11($b$) shows the recruitment of the inflammatory cells by the microcapsule, where images FIG. 11($a$) are representative tissue section images showing the tissue that locally comprised the opening-sealed microcapsule and where the cells were recruited, and diagram FIG. 11($b$) shows a quantitative analysis of the numbers of the cells recruited by each one microcapsule.

FIGS. 12($a$)-12($c$) shows the comparison of antigen utilization between different vaccine preparations, where diagram FIG. 12($a$) shows the numbers of the OVA positive cells, diagram FIG. 12($b$) shows the antigen endocytosis quantity in the OVA positive cells (expressed by mean fluoresence intensity), and diagram FIG. 12($c$) shows the utilization of antigen.

FIG. 13 shows a curve of pH variation in the local microenvironment during the degradation of the microcapsule in this disclosure.

FIG. 14 shows the ratio between MHC-I and MHC-II of $CD86^+$ DCs in acidic and neutral microenvironments.

DETAILED DESCRIPTION OF INVENTION

Vaccine

Figure 1:
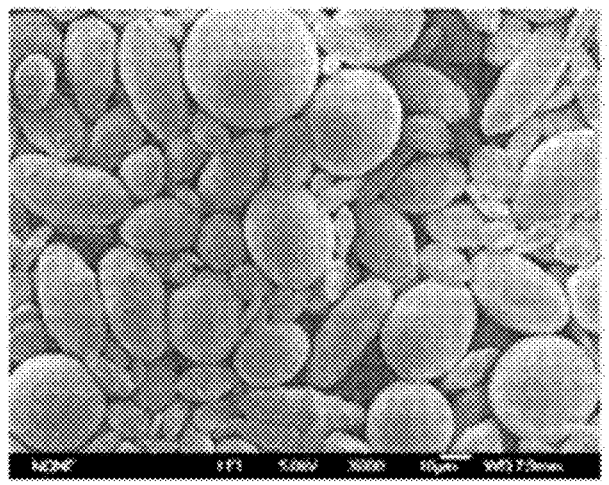
FIG. 1 is an SEM image of microspheres made of PLA.

The disclosure relates to a vaccine for the prophylactic or therapeutic treatment of diseases such as tumors in mammalian animals. The vaccine comprises an antigen and a matrix of a biodegradable polymer blend. The polymer blend comprises a hydrophobic polymer and an amphiphilic block copolymer. The vaccine exists in form of a microcapsule that comprises a multi-cavity structure inside, and has an average particle diameter of preferably 10-100 μm, more preferably 30-60 μm. The microcapsule is prepared by making a porous microsphere with penetrating channels from a polymer blend, mixing the porous microsphere with an antigen-containing solution, and sealing openings of the porous microsphere to form an opening-sealed microcapsule loading with antigen. The vaccine according to the disclosure may also comprise a pharmaceutically acceptable carrier, salt, or diluent.

In a preferred embodiment of the disclosure, the vaccine is an antitumor vaccine. The vaccine is simple to prepare, universally applicable to the prevention of recurrence and the suppression of metastasis and treatment for any kind tumor, and good in antitumor effects. After a subject is inoculated with the antitumor vaccine, the tumor antigen is first taken up and processed by antigen-presenting cells (APCs) to antigen peptides, which then combine with major histocompatibility complex (MHC) molecules on cell surfaces. APCs further transmit information of the peptides to T cells, and induce a subsequent immune response. In the process described above, most of the antigens are processed to peptides in the lysosome, which then combine with MHC-II molecules and are presented to $CD4^+$ T cells. More importantly, a few of the antigens can be processed to peptides by proteases in the cytoplasm, which then combine with MHC-I molecules, are presented to $CD8^+$ T cells and transform them into cytotoxic T lymphocytes (CTLs). Tumor lysis happens as a result of the fact that CTLs directly recognize and kill tumor cells, and also the fact that $CD4^+$ T cells and $CD8^+$ T cells jointly secrete cytokines to eliminate the tumor.

In a preferred embodiment of the disclosure, the antigen is a tumor antigen. Tumor antigens play an important role in the occurrence and development of tumors and in inducing the host antitumor immune effect, and they are the target molecules of tumor immunotherapy. Tumor antigens are divided into two categories according to their specificity: (1) tumor-associated antigens, which are antigens that are highly expressed in tumor tissues and are also expressed in normal tissues; and (2) tumor-specific antigens, which are only expressed in tumor tissues and do not exist in normal tissues and are thus safer in acting as tumor antigens. However, in the early stages of antitumor vaccine development, due to technological limitations, it was difficult to find and purify tumor-specific antigens and this restricts the wide application of antitumor vaccines. In recent years, with the development of the gene editing technology, researchers have discovered some specific antigens and neoantigens which may act as targets for antitumor vaccine immunity. This makes it possible to improve immune effects of vaccines by preparing personalized tumor antigens, and eventually solves the antigen selection problem. However, it is still difficult for suitable tumor antigens to activate an effective immune response. The main reason is that pure tumor antigens have a short half-life and are rapidly metabolized subsequent to the injection, which makes it hard for the host immune system to be effectively activated.

In some embodiments of the disclosure, the tumor antigen is obtained by collecting peptides from surface proteins of live tumor cells. The peptides are obtained by periodically adding protease that does not cause death of live primary tumor cells. For example, the tumor antigen can be obtained by subjecting live tumor cells previously eluted from the growth medium to primary culture, treating the tumor cells with protease without causing cell death, collecting the released surface tumor antigen, treating repeatedly the cells of primary culture with the protease in an interval (which is long enough for the activity of the surface tumor antigen to be restored by the cells), accumulating (enriching) the surface antigen to a dose sufficient for vaccination, and controlling components of the obtained surface tumor antigen.

In a preferred embodiment of the disclosure, the tumor antigen is, for example, mucin (MUC1), tumor membrane antigen, whole tumor cell antigen, or tumor neoantigen.

The antitumor vaccine of the disclosure may comprise one or more tumor antigens with the aim to generate one or more cytotoxic T lymphocyte clones which recognize specific antigenic peptide respectively, so as to cause more effective immune response. In the case of a plurality of tumor antigens, the tumor antigens are preferably selected to induce an immune response to tumors or tumor cells of one type.

In some embodiments of the disclosure, the antitumor vaccine is basically composed of a mixture of different antigens or a mixture of antigens and different immunostimulatory substances.

In tumor treatment, significantly activating CTLs and secreting Th1 cytokines can help the body attack and destroy tumors. When vaccine components are released, recruiting sufficient APCs for phagocytizing the vaccine is also crucial for eliciting an effective immune response. APCs are widely distributed in the various tissues of the body, so they play a vital role in spotting pathogenic microorganisms. In the peripheral tissue of skin, dangerous signals and antigens can be detected by Langerhans cells, DCs of other types, and macrophages; after being activated, they return to lymphatic organs and activate immune responses by presenting antigen information. The migration of these immune cells from peripheral tissues to lymphoid organs in the body is complicated and regulated primarily by many chemokines.

In a preferred embodiment of the disclosure, the antigen is a hepatitis B surface antigen, and the vaccine is a therapeutic hepatitis B vaccine.

Hepatitis B is a global infectious disease caused by the hepatitis B virus (HBV). Up to now, 2 billion people worldwide have been infected with the HBV, of whom about 350 million people are suffering chronic hepatitis B. There have been no effective medicaments for treating hepatitis B. Interferon and lamivudine, commonly used in antiviral therapy at present, can rapidly inhibit virus replication, but reoccurrence is prone to happen when the administration of them is ceased, and they can also lead to mutant strains.

In patients with chronic HBV infection, specific T cells are not much responsive due to their immune tolerance. The effect of the therapeutic vaccine is to enable cytotoxic T lymphocytes (CTLs), which are among main cells specific to a virus-clearing immune response, to play the cytolytic effect. That is, CTLs kill infected hepatocytes by releasing perforin or granzymes, or induce apoptosis of infected hepatocytes via a Fas-mediated pathway. However, studies of recent years have shown that a non-cytolytic mechanism participated by cytokines secreted by Th1 cells and CTLs plays a leading role in antiviral immunity. Cytokines such as IFN-α can inhibit virus replication and even clear viral DNA in a non-cytopathic manner. In particular, studies of IFN-γ in a variety of animal models have shown that it can inhibit HBV replication intermediates and HBV-specific mRNAs and plays an important role in virus clearance, viruses are eliminated by stimulating its own cellular immune response to promote the secretion of IFN-based cytokines.

Many types of hepatitis B surface antigens may be selected as the hepatitis B surface antigen in the disclosure. For example, hepatitis B surface antigens expressed by *Saccharomyces cerevisiae* and *Hansenula* yeasts and CHO hepatitis B surface antigens expressed by mammalian cell systems can be selected. However, hepatitis B surface antigens expressed by *Hansenula* yeasts are preferable. HbsAgs of different origins differ considerably in structure and property. Even with the same or similar gene codes, HBsAg particles expressed by different systems may still have different molecular sizes, molecular weights, and different subunit numbers, and then exhibit different charge, hydrophobicity, immunogenicity, etc.

In a preferred embodiment of the disclosure, the vaccine of the disclosure further comprises chemokines. Chemokines are a family of polypeptides having a molecular weight of 10 kDa and mainly act on related receptor families linked to G glycoprotein on cell surface. Chemokines and other molecules related to chemotactic attraction are locally generated, and then diffuse to form a soluble or solid concentration gradient. At this point, cells expressing chemokine receptors rely on information of the concentration gradient and arrive at where the chemotactic information originates.

Many chemokines are related to the migration of DCs and monocytes, including monocyte chemotactic protein-1 (MCP-1), monocyte chemotactic protein-2 (MCP-2), macrophage inflammatory protein-1α (MIP-1α), macrophage inflammatory protein-1β (MIP-1β), RANTE (regulated upon activation, normal T cell expressed and secreted), Complement C5a, β-defensin, and bacteria-derived formate peptides. Under normal circumstances, the proportion of DCs in peripheral tissues and blood is 1% or lower. Thus, if the vaccine can create a local base camp of chemokines, it can simulate and enhance the recruitment of DCs in vivo to the injection site by continuously releasing chemokines, thereby significantly enhancing the immune response.

In a preferred embodiment of the disclosure, the chemokine is, for example, macrophage inflammatory protein-3α (MIP-3α), monocyte chemotactic protein-1 (MCP-1) and GM-CSF, preferably GM-CSF. The chemokine is filled in the porous microsphere and sealed in the opening-sealed microcapsule by including the chemokine into the antigen-containing solution. In a preferred embodiment of the disclosure, the closed structure of the microcapsule chamber of the vaccine of the disclosure ensures that molecules filled in the opening-sealed microcapsule are effectively encapsulated in the cavity and thereby produce lasting and effective release. During the entire release, there is no abrupt release or plateau; the metabolism is slow and effective, achieving a metabolic rate as high as 90%, and almost all the antigen is released.

The excellent antigen-retention capability of the microcapsule ensures longer, lasting release of the antigen in the body. With the release of the antigen, the local retention of the microcapsule subsequent to injection leads to an inflammatory response, which in turn recruits inflammation-related cells to phagocytize the carrier and the released antigen. The kinetics of the release of the antigen and the polymeric matrix as an adjuvant is important in controlling the immune response and affects the final immune effect of the vaccine. When the kinetics of the release of the two are not synchronized—that is, when the antigen is released slowly, but the the adjuvant is released too fast or too slowly, the level of activation of APCs that locally phagocytize the vaccine is affected, making it difficult to activate an effective immune response.

Of the many APCs, DCs are the most powerful, specialized APCs in the body. According to their maturation and differentiation levels, DCs are divided into DC precursors, immature DCs, and mature DCs. DC precursors are cells that have not developed a DC phenotype or function in conditions of the normal mechanism. When the body is exposed to pathogenic microorganism infection or inflammatory stimuli, DC precursors are rapidly mobilized, differentiate and develop into immature DCs. Immature DCs account for most of DCs in conditions of the normal mechanism; they can efficiently ingest, process and present antigens and are rather capable of migration. Mature DCs, having been activated, are less capable of ingesting antigens but much more capable of presenting antigen information and stimulating activation of initial T cells. The opening-sealed microcapsule of the disclosure locally produces a large amount of DC chemokines, which is beneficial to the recruitment of more DCs. Consequently, antigens are processed and presented more effectively, and a more effective immune response is induced in the body.

In a preferred embodiment of the disclosure, the locally generated inflammatory microenvironment continuously recruits inflammation-related cells and APCs to the injection site, where they phagocytize the antigen. In this process, the secretion of chemokines plays a vital role in what types of cells and how many cells are recruited. The speed of degradation of the polymeric matrix which is the carrier and how the antigen is released significantly affect how much the chemokine is discharged.

In a preferred embodiment of the disclosure, both the antigen release and the cell recruitment act synergistically and work the best, so that the antigen released during the entire process is swallowed by cells which are most efficient in antigen presentation, namely immature DCs. Immature DCs are rather capable of phagocytizing a large number of antigens, which further improves the utilization of the antigen.

During the metabolism of the polymeric matrix which is the carrier, the locally generated inflammatory microenvironment continuously recruits inflammation-related cells and APCs to the injection site, where they phagocytize the antigen. In this process, the secretion of chemokines plays a vital role in what types of cells and how many cells are recruited. The speed of degradation of the carrier and how the antigen is released significantly affect how much the chemokine is discharged. In a preferred embodiment of the disclosure, the acidic microenvironment produced by the metabolism of the polymeric matrix which is the carrier significantly increases the number of cells recruited. Also, it has been found that the acidic microenvironment significantly improves the endocytosis of the antigen by the cells. The acidic microenvironment created by microcapsules such as polylactic acid acts like an immune adjuvant, and it is also an important factor in improving the utilization of the antigen by providing the activated DCs with a retention site. That is, without an additional vaccine adjuvant and multiple immunizations, the preferred embodiment of the disclosure can continuously provide activated APCs, which return back to lymph nodes. Additionally, the acidic microenvironment can significantly enhance antigen cross-presentation and the secretion of Th1 cytokines.

In a preferred embodiment of the disclosure, the vaccine comprises an immunostimulatory enhancer, such as mono-phosphoryl lipid A (MPLA), cytosine-guanine oligodeoxynucleotide, and/or polyinosinic acid.

Preparation of Microcapsule

In a preferred embodiment of the disclosure, the preparation of the microcapsule refers to a process in which a functional material is wrapped or dispersed in a shell material through a certain method to prepare a granular composite. Preferably, the microcapsule of the disclosure has a multi-cavity structure inside, and has an average particle size of 10-100 μm, preferably 20-80 μm, and more preferably 30-60 μm.

In a preferred embodiment of the disclosure, the porous microsphere has a porosity of at least 40% or more, for example at least 50% or more, preferably at least 60%, more preferably 70% or more, and has, for example, a pore diameter of of 1-5 μm. Preferably, the porous microsphere is prepared by a double-emulsion-and-solvent-removal method. The method makes it convenient to use a biodegradable polymer as the shell material and is suitable for the development of drug-loaded microcapsules. The porous microsphere has a through-hole structure, a multi-cavity internal structure, and a porous shell layer. Controlling the two dynamic processes of double emulsion evolution and double emulsion solidification makes it easy to control the opening structure and the number of openings of the porous microsphere. The subsequent step of immersing porous microsphere into a solution containing an antigen allows the antigen to enter the interior of the microsphere by diffusion. The openings of the porous microsphere can be sealed by the three methods of solvent swelling, irradiation, and heating-annealing.

In a preferred embodiment of the disclosure, the preparation of the microcapsule mainly comprises preparing porous microsphere, filling the porous microsphere with antigen, and sealing openings of the porous microsphere. Preferably, the method comprises the following steps:
(1) preparing an oil phase of a polymeric matrix solution in which the solvent is an organic solvent; preparing an inner water phase solution and an external water phase solution to which surfactant is added;
(2) dispersing the inner water phase into the oil phase to form a water-in-oil primary emulsion; dispersing the primary emulsion into the external water phase to form a water-in-oil-in-water double emulsion;
(3) solidifying the oil phase by a solvent removal method to obtain a porous microsphere having through-holes;
(4) mixing the porous microsphere with an antigen-containing solution to enable the antigen to enter inner cavities of the porous microsphere from its surface by diffusion mass transfer in the solution, thereby loading the porous microsphere with the antigen; and
(5) sealing the openings of the porous microsphere to form an opening-sealed microcapsule loaded with the antigen.

In a preferred embodiment of the disclosure, upon being prepared, the double emulsion undergoes an evolution process. During this process, the small droplets of the inner water phase in the double emulsion would gradually merge and become larger; at the same time, due to the difference in salt concentration between the inner and external water phases, the inner water phase would escape. Thus, during the evolution, the merging and escaping of the inner water phase proceed simultaneously. The merging of the inner water phase would bring about a porous structure inside the microsphere, and the escaping of the inner water phase would lead to a porous morphology on the surface of the microsphere. In a preferred embodiment of the disclosure, the polymeric matrix is a matrix of a biodegradable polymer blend that comprises a hydrophobic polymer and an amphiphilic block copolymer.

In a preferred embodiment of the disclosure, the hydrophobic polymer is lactide polymer (usually known as PLA), glycolide polymer, lactide-glycolide copolymer (usually known as PLGA), polycaprolactone, polyorthoester, and/or polyanhydride. Preferably it has a weight average molecular weight of 5,000-100,000 Daltons, more preferably 10,000-50,000 Daltons.

In a preferred embodiment of the disclosure, the hydrophilic block in the amphiphilic block copolymer is polyethylene glycol, polyacrylic acid, polyoxyethylene, and polyvinyl alcohol; the hydrophobic block in the amphiphilic block copolymer is a lactone copolymer or homopolymer. Preferably, the hydrophilic block is polyethylene glycol or poly(monomethoxyethylene glycol), and the hydrophobic block is polylactic acid (PLA) or a copolymer of lactic acid and glycolic acid (PLGA). In the amphiphilic block copolymer, the hydrophilic block has a weight average molecular weight of 500-30,000 Daltons, and the hydrophobic block has a weight average molecular weight of 500-50,000 Daltons. Preferably, the weight average molecular weight of the hydrophilic block is 1,000-20,000 Daltons, for example, 4,000-10,000 Daltons, and the weight average molecular weight of the hydrophobic block is preferably 5,000-20,000 Daltons.

In a preferred embodiment of the disclosure, the amphiphilic block copolymer is a copolymer of polyethylene glycol or monomethoxyethylene glycol with lactide and/or glycolide (usually known as PLGA). Preferably, it has a weight average molecular weight of 5,000-10,000 Daltons, more preferably 10,000-50,000 Daltons.

In a preferred embodiment of the disclosure, the amphiphilic block copolymer is useful in stabilizing the primary emulsion and thereby makes it possible to prepare a porous microsphere having a multi-cavity structure. The ratio, by weight, of the amphiphilic block copolymer to the matrix of the polymer blend is at least 5%, preferably at least 10%, at least 15%, at least 20%, at least 30%, at least 40%, or at least 50%. Because of its capability of eliciting a local inflammatory immune response, PLA is widely used in controlled release of drugs. PELA is a material better in biocompatibility and has been used more, and it is helpful in preparing porous microspheres with higher porosity. Changing the ratio between the two would result in a microsphere having improved hydrophobic properties and porosity, capable of adjusting the inflammatory response elicited by the carrier, and having improved biocompatibility.

In a preferred embodiment of the disclosure, the organic solvent in step (1) is an organic solvent that is volatile and immiscible with water, such as n-butanol, methyl ethyl ketone, ethyl ether, chloroform, tetrachloromethane, toluene, and the like. The organic solvent includes an organic solvent that is volatile and partially water soluble, such as ethyl acetate, phenol, and the like. More preferably, the organic solvent is one or a combination of at least two of alcohols, ketones, esters, ethers, alkylbenzenes, halogenated alkanes, and halogenated aromatic hydrocarbons that are not miscible with water. Typical but non-exhaustive examples of the combination are a combination of alcohols and ketones, a combination of alcohols, ketones, esters, and ethers, a combination of esters, alkylbenzenes, and halogenated alkanes, and a combination of esters, alkylbenzenes, halogenated alkanes, halogenated aromatic hydrocarbons, and so on. Particularly preferred is one or a combination of at least two of alcohols, esters, alkylbenzenes, chlorinated alkanes, and chlorinated aromatic hydrocarbons.

In a preferred embodiment of the disclosure, an immunostimulatory enhancer, such as monophosphoryl lipid A, is added to the organic solvent in step (1).

In a preferred embodiment of the disclosure, when the microsphere is loaded with the antigen, it is also loaded with an immunostimulatory enhancer, such as cytosine-guanine oligodeoxynucleotide and/or polyinosinic acid.

In a preferred embodiment of the disclosure, the solvent removal method in step (3) is a solvent extraction method; also, the solvent may be removed by volatilizing while standing still, by being stirred, or any other method.

In a preferred embodiment of the disclosure, in step (3) of solidifying, the inner water phase and the external water phase merge to form through holes.

In a preferred embodiment of the disclosure, the porous microsphere having through-holes in step (3) have a porous structure.

In a preferred embodiment of the disclosure, the porous microsphere of the disclosure has openings on its surface.

In a preferred embodiment of the disclosure, the porous microsphere has a porosity of at least 40% or more, for example at least 50% or more, preferably at least 60%, more preferably 70% or more, more preferably 80% or more. Preferably, the porous microsphere has openings having a diameter of 1-5 μm. Preferably, the openings inside the microsphere have a diameter ranging from 800 nm to 5 μm, and have an average diameter of about 1 μm.

In a preferred embodiment of the disclosure, in step (3), subsequent to solidifying the oil phase, the residual surfactant is removed, and it is particularly preferable to remove the residual surfactant by sieving or centrifugal washing.

In a preferred embodiment of the disclosure, the openings of the porous microsphere can be sealed by solvent swelling, irradiation, or heating-annealing. Also, those skilled in the art may seal the openings of the porous microsphere using their professional knowledge/new technology.

It should be appreciated by those skilled in the art that "sealing openings" herein means embedding, immobilizing or retaining the antigen and/or other substances such as chemokines inside the microcapsule. In the disclosure, sealing openings of the microcapsule does not mean that there is no opening on the surface of the microcapsule; instead it means that the antigen and/or other substances such as chemokines can be partially embedded, fixed or retained inside the microcapsule through the sealing process, and the antigen and/or other substances such as chemokines can be released from the microcapsule through, for example, the microcapsule degrading.

In a preferred embodiment of the disclosure, the heating-annealing method is an ideal sealing method. For example, the openings of the microsphere can be sealed using the unique self-healing characteristic of the matrix of a biodegradable polymer blend such as polylactic acid. In this method, molecules on the surface of the microsphere rearrange themselves after absorbing the energy of irradiation or heating, which leads to healing and sealing of the openings. For example, openings on the surface of the microsphere can be sealed by slowly heating the porous microsphere loaded with the antigen to a temperature proximate to the glass transition temperature of the microsphere, preferably, for example, 1-2° C. lower than the glass transition temperature of the microsphere, and after a period of time, slowly cooling the microsphere. During this process, the antigen is effectively encapsulated in the microcapsule at a stable loading or embedding rate. To seal openings of the microsphere by self-healing, it is necessary to heat the microsphere to a temperature proximate to its glass transition temperature, and the temperature also needs to be controlled to have no impact on the morphology of the microsphere.

In other embodiments of the disclosure, the porous microsphere can be prepared through phase separation of the polymer and a pore-forming agent. A solvent used in a pore forming process is usually known as a pore-forming agent, and an oil-soluble small molecule is usually used as a pore-forming agent. The phase separation of the polymer and the solvent may occur as the polymer chain is growing. As a result of an increase in the molecular weight of the polymer or the cross-linking between the molecules, the macromolecules are gradually precipitated out of the small-molecule solvent, appearing as a solid polymer. The phase separation may also occur in a polymer solution system in which due to change in environmental conditions, such as change in the temperature, the removal of a good solvent, or the addition of a poor solvent, the solvent's ability to dissolve the polymer decreases, which results in precipitation of the polymer.

One of the objectives of the disclosure is to provide a method for inducing a cytotoxic cell response to tumor cells or tumors in a patient. The method comprises administering to the patient an effective amount of a vaccine, preferably an antitumor vaccine, of the disclosure, especially by intravenous injection or infusion, preferably by intravenous infusion. The purpose of the method is especially to induce the activation of the patient's dendritic cells and $CD8^+$ cytotoxic cell response, and obtain specific $CD4^+$ helper and $CD8^+$ cytotoxic response.

The vaccine of the disclosure can be used for the prevention and treatment of diseases such as cancer or hepatitis such as hepatitis B, and more specifically for immunotherapy. The disclosure provides a method for prophylactically or therapeutically treating cancer or hepatitis such as hepatitis B, which comprises administering the vaccine to a mammalian subject in need thereof in a prophylactically or therapeutically effective amount.

In the disclosure, the term "immunization" means active immunization, that is, the induction of a specific immune response due to administration. The administration is, for example, administering in a small amount an antigen via subcutaneous, intradermal, intramuscular, oral, or nasal routes. The antigen is recognized as foreign by the vaccinated individual, so it is immunogenic in a suitable preparation. Therefore, the antigen is used as a "trigger" of the immune system to establish a specific immune response to the antigen.

According to the disclosure, immunization can be therapeutic or prophylactic. For example, it may provide preventive protection against the occurrence of cancer diseases by immunizing individuals who do not have cancer. An example of an individual to whom such preventive vaccination is applicable is an individual at an increased risk of developing cancer, though this application is not limited to such individuals. Patients at risk of cancer may have developed tumors, whether they are primary tumors or metastases, or may have shown a tendency to develop cancer.

In the disclosure, the term "an effective amount" means the amount of an antigenic/immunogenic composition that induces an immune response when administered to humans or animals. Those skilled in the art are able to determine with ease an effective amount by following conventional procedures.

The vaccine or pharmaceutical composition provided by the disclosure may be in the form of a sterile powder. For example, the sterile powder comprises the vaccine and mannitol. The sterile powder may be prepared by rinsing the microcapsule with water for injection, transferring the microcapsule to a dish for freeze drying, adding mannitol and water for injection in an appropriate amount to the microcapsule, and subjecting the mixture to freeze drying in a freeze dryer; and sieving the freeze-dried product and mixing it well, aseptically dividing the product into portions and placing them into containers, and capping the containers. Before administered to a patient, the sterile powder is suspended in an acceptable dispersing medium composed of water for injection, and one or more of a suspending agent, a pH adjusting agent, an isotonic regulator, and a surfactant. The suspending agent may be one or more of sodium carboxymethyl cellulose, polyvinyl alcohol, polyvinylpyrrolidone, sodium alginate, and glycerin. The isotonic regulator may be one or more of sodium chloride, glucose, mannitol, and sorbitol. The surfactant is a nonionic surfactant, such as polysorbates (such as polysorbate 80 and polysorbate 60).

The pharmaceutical composition such as the vaccine microcapsule provided by the disclosure may be administered to patients by approaches well known to those skilled in the art, such as an intraarterial, intravenous, percutaneous, intranasal, transbronchial, intramuscular or oral approach. The dosage and administration method vary according to the weight and age of the patient and the administration approach, which may be selected by those skilled in the art as needed.

A liquid pharmaceutical composition is generally formulated to have a pH between about 3.0 and 9.0, more preferably between about 4.5 and 8.5, and still more preferably between about 5.0 and 8.0. The pH of the composition may be maintained by a buffer solution such as acetate, citrate, phosphate, succinate, Tris or histidine. The concentration of the buffer solution usually ranges from about 1 mM to 50 mM. The pH of the composition may alternatively be adjusted by physiologically acceptable acid or base.

The pharmaceutical composition is administered to an individual in a prophylactically effective amount or a therapeutically effective amount (as the case may be, although prevention can be regarded as a treatment), which is sufficient to show benefit to the individual. Generally, this will result in a therapeutically useful activity that is beneficial to the individual. The actual amount of the compound administered, as well as the rate and time course of the administration, will depend on the nature and severity of the condition being treated. Treatment prescriptions such as dosage decisions are within the responsibilities of general practitioners and other doctors, and usually consider the condition being treated, the individual patient's condition, the administration site, the method of administration, and other factors known to the doctor.

The embodiments disclosed herein are meant to illustrate several aspects of the disclosure.

Comparative Example 1 Porous Microsphere Made of PLA 100 mg of racemic carboxyl-terminated polylactic acid having a molecular weight of 20,000 Daltons (PLA, Jinan Daigang Bioengineering Co., Ltd.) were dissolved in 2 mL of ethyl acetate (oil phase, O). After 0.5 mL of 0.05% sodium chloride aqueous solution (inner water phase W1) were added, a primary emulsion (water-in-oil, W1/O) was prepared using an ultrasonic disintegrator. Then, the primary emulsion was poured into 15 mL of an aqueous solution (external water phase W2) containing PVA (purchased from Japan's Kuraray), and a double emulsion (water-in-oil-in-water, W1/O/W2) was prepared through emulsification by a homogenizer. The double emulsion was suspended in a vertical suspension apparatus for 25 min to evolve. Subsequently, the double emulsion was poured into 500 mL of ultrapure water and magnetically stirred (500 rpm) at room temperature for 10 min, resulting in solidification of microspheres. Finally, the microspheres were centrifuged several times (500 g, 5 min), and the supernatant was discarded while the microspheres at the bottom of the tube were collected. 1 mL of ultrapure water was added to the microspheres, and they were stored at 4° C.

50 μL of the PLA microsphere suspension were pipetted onto tin foil, and dried at room temperature. The sample-containing tin foil was pasted on the sample preparation table using conductive adhesive, and gold was sprayed onto the sample for observation of the morphology of the microspheres by SEM. The prepared PLA microspheres are illustrated in FIG. 1. As shown in FIG. 1, the microspheres, made only of PLA, did not have an apparent porous structure, so they were not suitable as the porous microsphere of the disclosure and thus not suitable for the further development of the opening-sealed microsphere of the disclosure.

Example 1 Porous Microsphere Made of PLA and PELA 95 mg of racemic carboxyl-terminated polylactic acid having a molecular weight of 20,000 Daltons (PLA, Jinan Daigang Bioengineering Co., Ltd.) and 5 mg of a copolymer having a molecular weight of 38,000 Daltons (PELA, purchased from Jinan Daigang Biological Engineering Co., Ltd.) of polyethylene glycol (mPEG, Mw: 2000) and racemic carboxyl-terminated polylactic acid (PLA, Mw: 36000) were dissolved in 2 mL of ethyl acetate (oil phase, O). After 0.5 mL of 0.05% sodium chloride aqueous solution (inner water phase W1) were added, a primary emulsion (water-in-oil, W1/O) was prepared using an ultrasonic disintegrator. Then, the primary emulsion was poured into 15 mL of an aqueous solution (external water phase W2) containing PVA, and a double emulsion (water-in-oil-in-water, W1/O/W2) was prepared through emulsification by a homogenizer. The double emulsion was suspended in a vertical suspension apparatus for 25 min to evolve. Subsequently, the double emulsion was poured into 500 mL of ultrapure water and magnetically stirred (500 rpm) at room temperature for 10 min, resulting in solidification of microspheres. Finally, the microspheres were centrifuged several times (500 g, 5 min), and the supernatant was discarded while the microspheres at the bottom of the tube were collected. 1 mL of ultrapure water was added to the microspheres, and they were stored at 4° C.

Figure 2:
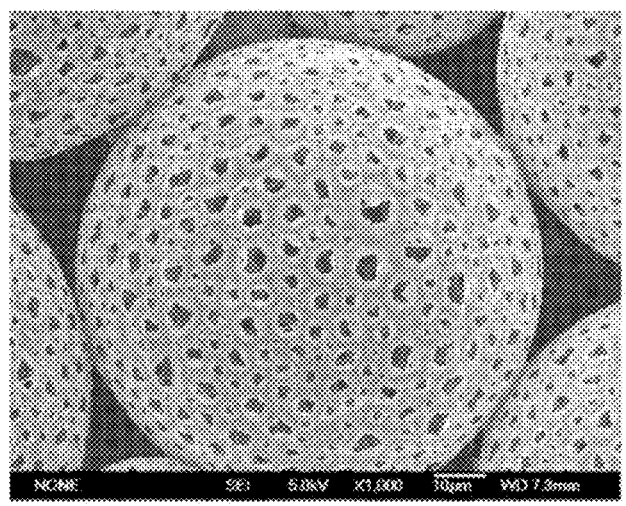
FIG. 2 is an SEM image of microspheres made of PLA and PELA.
Figure 3:
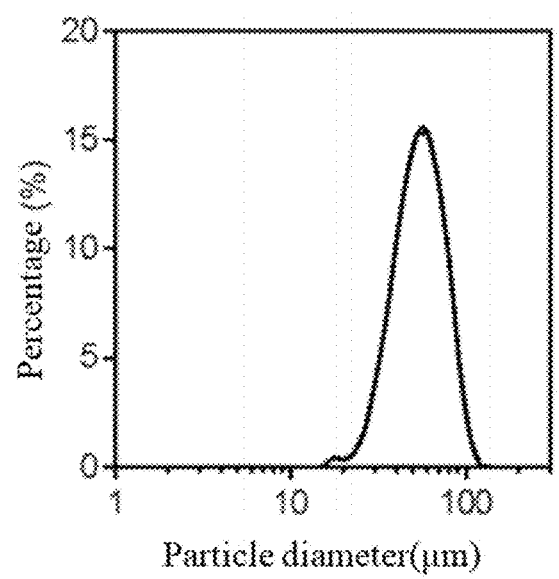
FIG. 3 is a diagram of the particle size distribution of the microspheres made of PLA and PELA.
Figure 4:
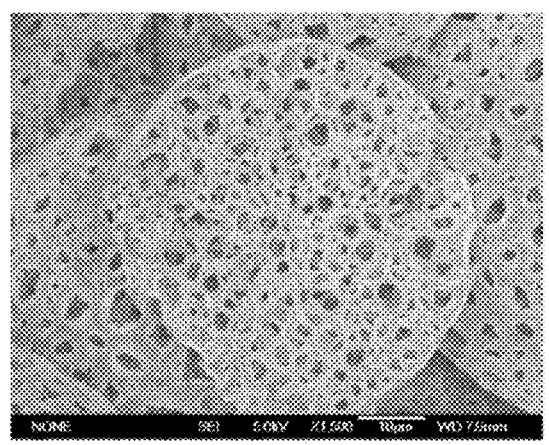
FIG. 4 is an SEM image of the internal structure of the microspheres made of PLA and PELA.

50 μL of the microsphere suspension were pipetted onto tin foil, and dried at room temperature. The sample-containing tin foil was pasted on the sample preparation table using conductive adhesive, and gold was sprayed onto the sample for observation of the morphology of the microspheres by SEM. As shown in FIG. 2, openings having an average size of 1-2 μm exist on the surface of the microsphere. The particle size distribution of the microspheres is shown in FIG. 3, and they had an average particle size of 60 μm. To observe the internal structure of the microspheres, the dried microspheres were cut with an ultra-thin blade. Then, sample was adhered to conductive glue, and gold was sprayed onto the sample for SEM observation. As shown in FIG. 4, the microspheres had internal pores communicating with each other, and the pores had a diameter of about 1-5 μm.

Figure 5:
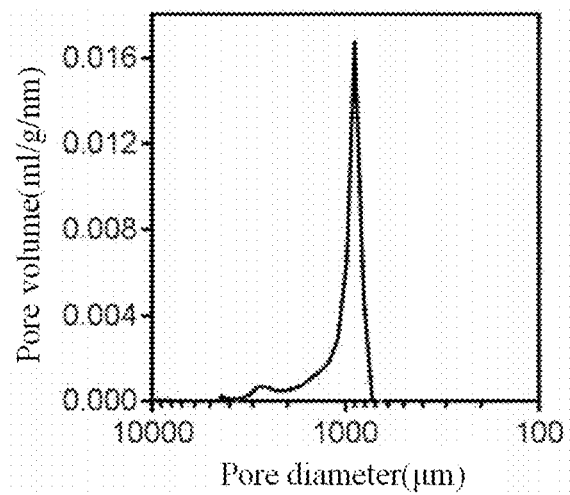
FIG. 5 is a diagram of the internal pore size distribution of the microspheres made of PLA and PELA.

30 mg of the freeze-dried porous microspheres were measured by a mercury porosimeter, and the measurement was performed in parallel three times. The porosity of the porous microspheres was calculated to be 82%, and the average pore size distribution was also calculated. As shown in FIG. 5, the size of the pores inside the microspheres ranged from 800 nm to 5 μm, and they had an average pore size of about 1 μm.

Example 2 Preparation of Opening-Sealed Microcapsule Loaded with Antigen 1 mL of the porous microspheres suspension prepared in Example 1, which had a dry weight of 30 mg, was pipetted into a 1.5 mL centrifuge tube. After the suspension was centrifuged, the supernatant was discarded, and 500 μL of OVA (purchased from Sigma) at a concentration of 50 mg/mL or 10 mg/mL, or 500 μL of MUC1 (purchased from Gil Biochemical Shanghai Co., Ltd.) at a concentration of 8 mg/mL were blend with the microspheres. The mixture was suspended (300 rpm) in a vertical suspension apparatus for 4 h, allowing the protein or peptide to fully enter the cavity of the microsphere via the pores inside the microsphere. The vertical suspension apparatus together with the microspheres were heated in a thermostat at 39° C., allowing the openings on the microspheres were sealed. The suspension speed in the thermostat was 100 rpm, which ensured that the microspheres were evenly heated without sedimentation during the entire heating process. Two hours later, the sealing was completed. The suspension was centrifuged (500 g, 5 min), and the supernatant was removed, resulting in opening-sealed microcapsules loaded with protein or peptide molecules.

Figure 6:
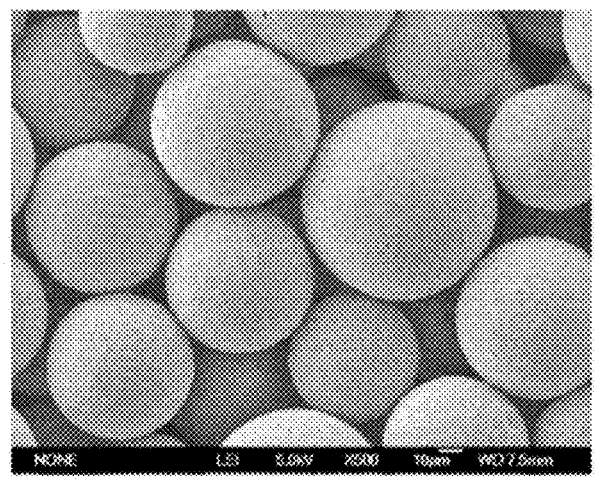
FIG. 6 is an SEM image of the opening-sealed microcapsule according to the disclosure.
Figure 7:
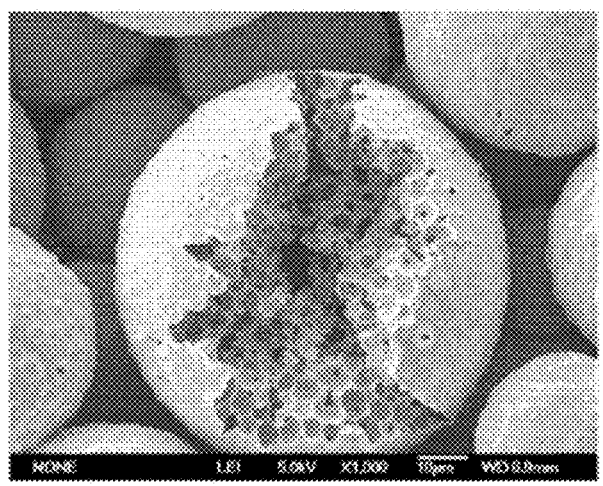
FIG. 7 shows an internal structure of the opening-sealed microcapsule according to the disclosure.

50 μL of the opening-sealed microcapsules loaded with OVA were pipetted onto tin foil, and dried at room temperature. The sample-containing tin foil was pasted on the sample preparation table using conductive adhesive, and gold was sprayed onto the sample for observation of the morphology of the microcapsules by SEM. As shown in FIG. 6, the openings on the surface were all sealed, demonstrating the formation of opening-sealed microcapsules. To observe the internal structure of the microcapsules, the dried microcapsules were cut with an ultra-thin blade. Then, the sample was adhered to conductive glue, and gold was sprayed onto the sample for SEM observation. As shown in FIG. 7, the microcapsules still had internal pores with a diameter of 1-5 μm, but the internal pores were closed and independent of each other, instead of communicating with each other.

The following is a description of how the loading rate and embedding rate of OVA or MUC1 as well as their contents in the microcapsules were measured.

To extract OVA in the opening-sealed microcapsules, 1 mL of 0.1 M sodium hydroxide aqueous solution was added to 5 mg of the lyophilized microcapsules loaded with OVA (n=3), the mixture was placed at 4° C. for 12 h to allow the microcapsules to degrade completely. After the mixture as centrifuged, the supernatant was taken out and 0.1 M hydrochloric acid was added thereto to let the solution become neutral. 100 μL of the supernatant were pipetted into the BCA kit to detect the protein content.

To extract MUC1 in the opening-sealed microcapsules, 300 μL of acetonitrile were added to 5 mg of the lyophilized microcapsules loaded with MUC1 (n=3) to completely dissolve the microcapsules. After the system became clear, 1.7 mL of 0.015 M HCl solution was added. Insoluble substances and impurities in the system were removed by a 0.45 μm filter membrane. The concentration of MUC1 was determined by RP-HPLC. The chromatography conditions were as follows:

Mobile phase A was 0.1% trifluoroacetic acid in deionized water, and mobile phase B was 0.1% trifluoroacetic acid in HPLC-grade acetonitrile. The elution gradient was 0%-60% of mobile phase B over 0-25 min. The flow rate was 1.0 mL/min. The detecting wavelength was 220 nm.

The final loading rate (%) of the antigen (OVA/MUC1) in the opening-sealed microcapsule was calculated by dividing the mass of the antigen in the opening-sealed microcapsule by the mass of the microsphere (dry weight) and then being multiplied by 100%. The embedding rate (%) of the antigen (OVA/MUC1) in the opening-sealed microcapsule was calculated by dividing the mass of the antigen in the opening-sealed microcapsule by the mass (the concentration multiplied by the volume) of the antigen prior to the loading and then being multiplied by 100%.

Figure 8:
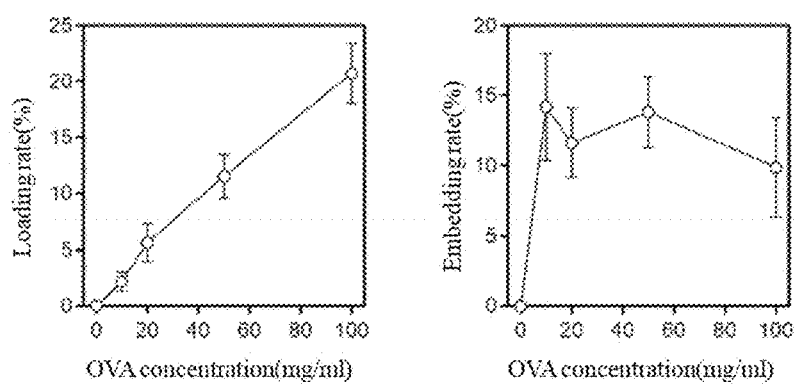
FIG. 8 shows the loading rate and embedding rate of the antigen OVA in the opening-sealed microcapsule according to the disclosure.

As shown in FIGS. 8 and 9, as the concentrations of OVA and MUC1 increase, the loading rates show a linear increase trend. When the concentration of the antigen is 100 mg/mL, the loading rate is 20%. As as the concentrations of OVA and MUC1 increase, the embedding rates were at a relatively stable level, indicating that the embedding rate of the microcapsules depends only on the cavity volume of the microcapsules. The linearly increased loading rate and the relatively stable embedding rate help to regulate the ratio of the antigen to the microcapsules, making it possible to meet the needs of different loading systems.

Example 3 Preparation of Opening-Sealed Microcapsule Loaded with Antigen and MPLA 1 mg of MPLA (purchased from Sigma) was dissolved in 500 μL of chloroform ($CHCl_3$), and then 100 μL of the chloroform solution were added to 1.9 mL of ethyl acetate, giving an oil phase. 95 mg of racemic carboxyl-terminated polylactic acid having a molecular weight of 20,000 Daltons (PLA, Jinan Daigang Bioengineering Co., Ltd.) and 5 mg of a copolymer having a molecular weight of 38,000 Daltons (PELA, purchased from Jinan Daigang Biological Engineering Co., Ltd.) of polyethylene glycol (mPEG, Mw: 2000) and racemic carboxyl-terminated polylactic acid (PLA, Mw: 36000) were dissolved in 2 mL of the oil phase containing chloroform and MPLA. After 0.5 mL of 0.05% sodium chloride aqueous solution (inner water phase W1) were added, a primary emulsion (water-in-oil, W1/O) was prepared using an ultrasonic disintegrator. Then, the primary emulsion was poured into 15 mL of an aqueous solution (external water phase W2) containing PVA, and a double emulsion (water-in-oil-in-water, W1/O/W2) was prepared through emulsification by a homogenizer. The double emulsion was suspended in a vertical suspension apparatus for 25 min to evolve. Subsequently, the double emulsion was poured into 500 mL of ultrapure water and magnetically stirred (500 rpm) at room temperature, resulting in solidification of microspheres. Finally, the microspheres were centrifuged several times (500 g, 5 min), and the supernatant was discarded while the microspheres at the bottom of the tube were collected. 1 mL of ultrapure water was added to the microspheres, and they were stored at 4° C.

The opening-sealed microcapsules loaded with antigen and MPLA were prepared as follows: 1 mL of the suspension of the microspheres loaded with MPLA was pipetted into a 1.5 mL centrifuge tube. After the suspension was centrifuged, the supernatant was discarded, giving the microspheres having a volume of 500 μL. 500 μL of OVA (purchased from Sigma) at a concentration of 10 mg/mL, or 500 μL of MUC1 (purchased from Gil Biochemical Shanghai Co., Ltd.) at a concentration of 8 mg/mL were blend with the microspheres. The mixture was suspended (300 rpm) in a vertical suspension apparatus for 4 h, allowing the protein or peptide to fully enter the cavity of the microsphere via the pores inside the microsphere. The vertical suspension apparatus together with the microspheres were heated in a thermostat at 39° C. Two hours later, the sealing was completed. The suspension was centrifuged (500 g, 5 min), and the supernatant was removed, resulting in opening-sealed microcapsules loaded with antigen and MPLA. It was calculated that the loading rate of OVA, the loading rate of MUC1, and the loading rate of MPLA in the microcapsules were 2%, 1.7%, and 1% o.

Example 4 Preparation of Opening-Sealed Microcapsule Loaded with Chemokine

The porous microspheres suspension prepared in Example 2 which had a dry weight of 30 mg was pipetted into a 1.5 mL centrifuge tube. After the suspension was centrifuged, the supernatant was discarded, giving the microspheres having a volume of 500 μL. 500 μL of GM-CSF (purchased from Peprotech) solution at a concentration of 1 mg/mL were blend with the microspheres. The mixture was suspended (300 rpm) in a vertical suspension apparatus for 4 h, allowing the chemokine to enter the cavity of the microsphere. The vertical suspension apparatus together with the microspheres were heated in a thermostat at 39° C. Two hours later, the sealing was completed. The suspension was centrifuged, and the supernatant was removed, resulting in opening-sealed microcapsules loaded with the chemokine. It was calculated that the loading rate of GM-CSF in the microcapsules was 2.4% 0.

Example 5 Synergy Between Release of Antigen and Recruitment of Cells 6-8 weeks old female C57BL/6 mice (n=4, purchased from Beijing Weitong Lihua Experimental Animal Co., Ltd.) were divided into three groups that were injected subcutaneously with different vaccine preparations on the back. The three groups consist of a group injected with the preparation of a simple fluorescent antigen (in which OVA was labeled with dye Cy5), a group injected with the preparation of a blend of a fluorescent antigen and the porous microsphere, and a group injected with the preparation of a fluorescent antigen encapsulated in the opening-sealed microcapsule. The injection doses of the microsphere and the antigen in all the groups were 3 mg and 60 μg, respectively. In different stages of the metabolism (1 h, 2 h, 4 h, 8 h, 0.5 d, 1 d, 2 d, 4 d, 7 d, 10 d, 14 d, 17 d, 21 d, 25 d, and 30 d), an in vivo imaging system was used to observe the different metabolic behaviors of the antigen in the porous microsphere and in the opening-sealed microcapsule.

As shown in FIG. 10, the local fluorescence intensity of OVA in the simple antigen group was almost zero on the 3rd day, indicating that the antigen was metabolized very fast, and almost all of it was metabolized on the 3rd day. In the blend group 50% of OVA were suddenly released within 24 h. That was because in the early stage of the metabolism, the free antigen outside the microspheres was rapidly metabolized by the tissue. The antigen in the porous microspheres, however, was still released after 24 hours, and still showed strong fluorescence intensity on the 5th day. It can be seen from FIG. 10 that 10% of the antigen were not metabolized. The reason was that the local retention of the antigen by the microsphere and the retarding of it by the pores prolonged the metabolism of the antigen so much that it took a total of about 7 days to metabolize all of the antigen. The comparison showed that the embedding group maintained strong fluorescence intensity during the two weeks of the testing. As shown in the quantitative graph, there was no sudden release of the antigen in the early stage of the metabolism, and 10% of the antigen was released within 24 hours and only 20% of the antigen was metabolized in 3 days. The reason was that openings on the surface of the microcapsules were closed, and only via the nanopores on the surface of the material was the antigen slowly released from within the microcapsules. As the time went on, the surface and internal structures of the carrier changed, leading to the release of a large amount of the antigen in the microcapsule and the release of about 50% of the antigen in 7 days. Subsequently, the metabolism slowed down, and 14 days later, strong fluorescence intensity could still be seen. As shown in FIG. 10, there were 35% of the antigens that were not metabolized.

After the microcapsules were injected, the in situ retention of the microcapsules along with the release of the antigen led to an inflammatory response, which then recruited inflammation-related cells to phagocytize the carrier and the released antigen. In order to further observe the cell recruitment, 6-8 weeks old female C57BL/6 mice (n=4, purchased from Beijing Weitong Lihua Experimental Animal Co., Ltd.) were on the back with the blank opening-sealed microcapsules prepared in Example 2. Mice were killed at different times of the metabolism. The portion of the mouse's back where the microcapsule was injected was opened, and the local subcutaneous tissue enclosing the carrier was taken out with tweezers. The tissue was cut with scissors, and it was soaked in 4% formalin solution for 24 hours. Then, the tissue was embedded with paraffin and subjected to sectioning, hematoxylin & eosin (H&E) staining and mounting, so as to obtain H & E stained samples. Finally, the slides were scanned using the Automated Quantitative Pathology Imaging System (Vectra 3.0, purchased from PerkinElmer) for the observation of the inflammatory response at the injection site.

As shown in FIG. 11a, on the 3rd day, the cells (dark dots) were gradually recruited around the microcapsules (light-colored rounds). As the degradation went on, the cells around the microspheres continued to increase, and the inflammation became so strong that infiltration of the inflammatory cells could be seen even inside some microcapsules. The number of the dots and the number of the microcapsules were counted using the Inform software so that the number of cells recruited locally by each microcapsule was calculated. As shown in FIG. 11b, on the 14th day each microsphere recruited an average of about 20 cells. It can therefore be concluded that during the entire metabolic process, the local inflammatory response gradually increased due to the accumulation of the products of the degradation. Besides, no redness, swelling, granulation, or pus was found in the local tissues during the dissection of the mice, which indicated that the inflammatory response induced by the the opening-sealed microcapsule was safe.

6-8 weeks old female C57BL/6 mice (n=4, purchased from Beijing Weitong Lihua Experimental Animal Co., Ltd.) were divided into three groups that were injected with different vaccine preparations on the thigh muscle. The three groups consisted of a group injected with the preparation of a simple Cy5 dye-labeled OVA (Cy5-OVA) group, a group injected with the preparation of a blend of Cy5 dye-labeled OVA and the porous microsphere, and a group injected with the preparation of Cy5 dye-labeled OVA encapsulated in the opening-sealed microcapsule. Five days later, the mice were killed, and their muscle tissues containing the microspheres were taken out, cut into small pieces with scissors, ground into a suspension, resuspended in PBS at 4° C., and centrifuged to remove the supernatant. To the centrifugal residue, was added 1 mL of a solution of an enzyme mixture (made by dissolving collagenase D and 100 U/mL recombinant DNase I in RPMI 1640 medium) at a concentration of 1 mg/mL. The mixture was incubated at 37° C. for 30 min, washed with PBS, and subjected to filtration with a 20 μm cell sieve to get rid of impurities, giving a single-cell suspension. By following the flow cytometry sample staining procedures, anti-mouse FITC-CD11c and eFlour450-F4/80 fluorescent antibodies were added to the samples to label the DCs and macrophages. The BD LSRFortessa flow cytometer was used to detect $OVA^+$ cells, CD $11c^+OVA^+$ cells, and $F4/80^+OVA^+$ cells, and the data was analyzed using the Flowjo software.

As shown in FIG. 12, in the simple antigen group (control group), the number of $OVA^+$ cells was small, and the fluorescence intensity of intracellular OVA was very weak, indicating that the local antigen was almost completely metabolized on the 5th day. In the blend group, the antigen-retention capability of the microsphere significantly increased the utilization of the antigen by about 20 times, the number of $OVA^+$ cells by about 10 times, and the endocytosis of OVA by 2 times. In the embedding group, as a result of the excellent antigen-retention capability and antigen-release capability, the number of $OVA^+$ cells increased by about 50 times, the endocytosis of OVA increased by 4 times or more, and the utilization of the antigen increased by 200 times or more. The above results showed that the opening-sealed microcapsule regulated antigen release and cell recruitment more effectively and coordinated antigen release and cell recruitment, thereby improving the utilization of antigen. The utilization of the antigen was calculated by normalizing the number of $OVA^+$ cells multiplied by the fluorescence intensity using the utilization of the antigen of the simple antigen group. The synergy not only promoted more cells to phagocytize the antigen, but also increased the endocytosis of the antigen, thereby maximizing the utilization of the antigen.

Example 6 Effect of Acidic Microenvironment of Opening-Sealed Microcapsule on Cell Recruitment Lactic acid, the product of the degradation of the polylactic acid microcapsule, causes acidification of the local microenvironment. The degree, change, and duration of the acidification may affect the subsequent immune response. Therefore, it is necessary to accurately monitor the acidification process and changes of the local microenvironment. SNARF®-1 is a pH sensitive probe capable of monitoring pH ranging from 6 to 9. It is used by exciting the dye at a wavelength about 488 nm, while monitoring the fluorescence emission at the two wave lengths of about 580 nm and 640 nm. The ratio of the fluorescence intensities from the dye, i.e., 1640/1580, corresponds to pH. The smaller the ratio, the lower the pH of the system is. Therefore, it is possible to monitor in real time the change in pH of the local microenvironment that is caused by lactic acid, the product of the degradation of the polylactic acid microcapsule, by loading the microcapsule with SNARF®-1 and observing with a confocal laser scanning microscope.

Specifically, female C57/BL6 mice (n=6) were injected subcutaneously with the opening-sealed microcapsule in which SNARF®-1 has been embedded, on the back. The mice were killed on the 3rd, 5th, 7th, and 14th days. The subcutaneous tissue enclosing the microspheres was taken out and was placed under a confocal laser scanning microscope for the observation of changes in pH of the local tissue. The fluorescence image was observed; the fluorescence intensity ratio 1640/1580 was calculated, and the actual pH was calculated in light of the standard curve.

The experiment found that three days after the metabolism, the local microenvironment changed from neutral to acidic. As shown in FIG. 13, the local pH changed from 7.2 to 6.5. As the material was metabolized continuously, no further acidification of the local acidic environment was found, and instead the pH was maintained at about 6.5, which meant that there was no accumulation of lactic acid that was otherwise caused by the gradual degradation of ordinary non-porous polylactic acid microspheres. When ordinary non-porous polylactic acid microspheres degrade inside and outside, lactic acid produced by the degradation inside the microsphere accumulates due to the hindered mass transfer, which results in an internal pH lower than the pH outside the microsphere and may cause a sudden drop or instability in pH. The opening-sealed microcapsule of the disclosure, because of the internal pores communicating with each other, effectively avoids the above-mentioned problems and makes it possible for lactic acid produced by the degradation of the internal material to efficiently go outside. When the metabolism of lactic acid by the body and the generation of lactic acid from the degradation of polylactic acid achieve a dynamic balance in the body, the local pH is maintained at a relatively stable level, thereby creating a relatively stable microenvironment for the local cells to perform functions. This stable state helps to analyze how the local cells are affected.

When physiological inflammation occurs, usually a large number of cells are recruited at the inflammation site, and at the same time the inflammation site is acidified. It is thus assumed that acidity is related to cell recruitment. Therefore, the inventors investigated the influence of neutral microenvironment (NM) and acidic microenvironment (AM) on cell recruitment. To compare with AM, NM can established by loading the microcapsule with the basic salt $NaHCO_3$, a salt formed between a weak acid and a strong base, because it can neutralize lactic acid generated by the degradation of the microcapsule.

The acidic environment improves the utilization of the antigen by enhancing cell recruitment and stimulating the endocytosis of the antigen. This also suggests that only the synergy between antigen release and cell recruitment can improve the utilization of the antigen. For example, a favorable microenvironment that stimulates immune cells to phagocytize the antigens in large quantities is needed to further improve the utilization of the antigen. Therefore, multiple factors such as antigen release, cell recruitment, the number and type of DCs, and the acidic microenvironment that stimulates the endocytosis are required to maximize the utilization of the antigen. The blend group and the embedding group loaded with $NaHCO_3$ indicate that any one of the aforementioned factors is indispensable. Only the opening-sealed microcapsule of the disclosure can mobilize all the factors and let them function in concert so that the antigen can be used most efficiently.

After DCs phagocytize the antigen, the antigen is processed into antigen peptides, which are expressed on the surface of APCs in the form of an antigen peptide-major histocompatibility complex (MHC) for T cells to recognize. However, if APCs phagocytize the antigen in the absence of a stimulus, they will fail to activate T cells by effectively expressing costimulatory molecules (CD80, CD86, CD40). In most cases, after DCs phagocytize an exogenous antigen, they process and present the antigen mainly through the lysosome pathway. This process is restricted by MHC-II molecules and mainly mediates T cell humoral immune-related reactions. In some special cases, an exogenous antigen can be presented through the cytosol pathway, i.e., the MHC-I molecule pathway, by which cytotoxic T lymphocytes (CTLs) are activated directly and the target cells are killed most directly and effectively. Therefore, for therapeutic tumor vaccines, more of the antigens need to be presented via MHC-I molecules so that tumors are killed more effectively.

An acidic environment can significantly improve the endocytosis of the antigen by APCs, especially by DCs. However, the activation of APCs, the number of the presented antigens, and the pathways of the presentation need further investigation. Here is a description of how the investigation was done. First, OVA was dissolved in a solution of 20 mM $NaHCO_3$ and a solution of PBS respectively. The opening-sealed microcapsules were prepared by following the method of loading the antigen described above. The opening-sealed microcapsules were injected into the thigh muscles of female C57BL/6 mice (n=6, purchased from Beijing Weitong Lihua Experimental Animal Co., Ltd.), 6-8 weeks old. The tissue that healed and enclosed the microcapsules was taken out after the mice were dissected on the 5th day. The tissue was cut into pieces with scissors, added to 1 mL of a solution of an enzyme mixture (made by dissolving 1 mg/ml collagenase D and 100 U/mL recombinant DNase I in RPMI 1640 medium), and incubated at 37° C. for 30 min. Then, the mixture was homogenized in a cell homogenizer to make a single-cell suspension, and centrifuged to remove the supernatant. The cells were collected, subjected to filtration with a 20 µm cell sieve to remove impurities, and counted with a handheld cell counter. By following the flow cytometry sample staining procedures, PE-CD11c, APC-CD80, APC-Cy7-CD86, eFlour 450-MHC-I, and BV 655-MHC-II were used to label the DC surface costimulatory molecules and the MHCs so as to detect the amount of DCs that were locally activated.

As shown in FIG. 14, DCs were significantly activated in the acidic environment. The expression level of MHC-I molecules in CD86 DC was 40 times that of MHC-II, indicating that DCs presented the antigen more via MHC-I than via MHC-II. This was an indicator that the microcapsules were capable of efficiently promoting cross-presentation of the antigen. However, the percentage of MHC-I in CD86 DC in the neutral environment decreased by one time or more, indicating that the environment played an important role in the microcapsule promoting the cross-presentation of the antigen.

Example 7. Effect of Opening-Sealed Microcapsule on E.G7 Lymphoma Solid Tumor in Animal To construct E.G7 tumor-bearing mice models, $1\times10^6$ E.G7 tumor cells (purchased from ATCC) were injected into 6-8 weeks old female C57BL/6 mice (purchased from Beijing Weitonglihua Experimental Animal Co., Ltd.) on the armpit, and the tumor-bearing mice were randomly divided into groups each consisting of 6 mice. The mice were vaccinated when the tumor grew to a volume of 50-60 mm$^3$ on the 4th day. The six groups of mice were vaccinated respectively as follows: a group was inoculated with PBS, a group was inoculated with low-dose OVA several times (in which 20 µg of OVA was additionally inoculated on the 7th and 14th days), a group was inoculated with high-dose (60 µg) OVA a single time, a group was inoculated with a blend of the porous microsphere (3 mg) and OVA (60 µg), a group was inoculated with the opening-sealed microcapsule loaded with OVA (which was prepared as in Example 2 and comprised 3 mg of the microsphere and 60 µg of OVA), and a group was inoculated with the opening-sealed microcapsule loaded with OVA and MPLA (which was prepared as in Example 3 and comprised 3 mg of the microsphere, 60 µg of OVA, and 3 µg of MPLA). From the day the tumor models were constructed, the mice were observed for the hair, weight, and survival, and the length and width of the tumor were measured with a vernier caliper, every other day. The volume of the tumor was calculated by this formula: $V=1/2 \times L \times W^2$ (where L is the length of the tumor, and W is the width of the tumor).

Figure 15:
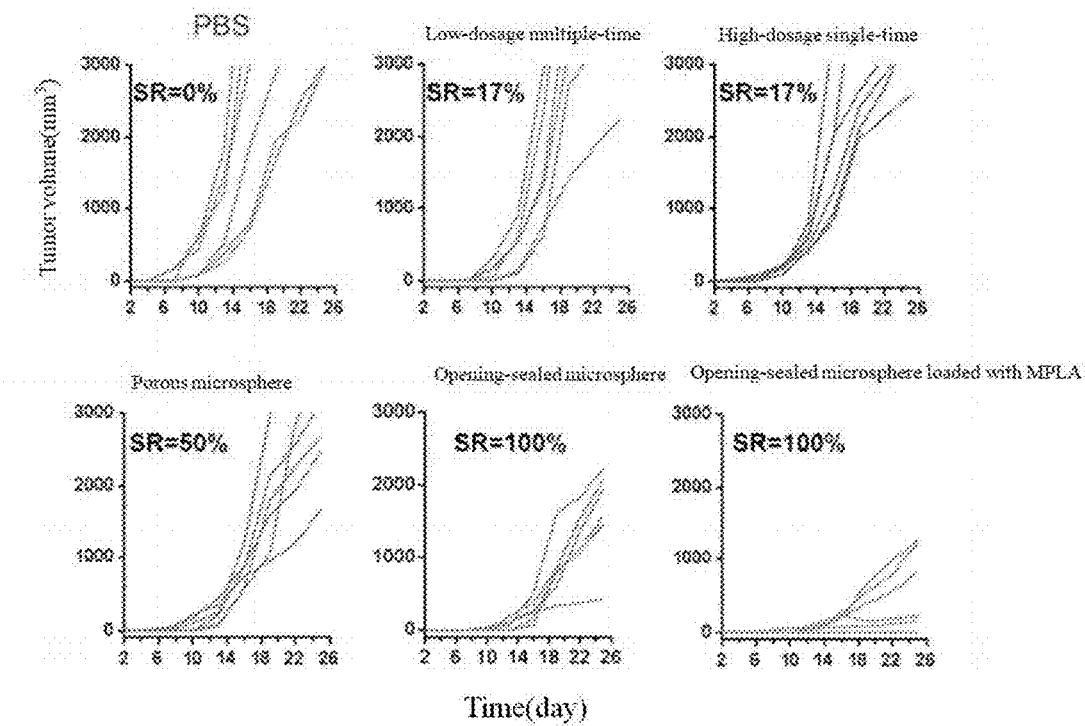
FIG. 15 shows tumor growth curves of E.G7 tumor-bearing mice with different vaccinations.

As shown in the tumor growth curve in FIG. 15, in the two groups inoculated with only OVA, the growth of the tumor was not inhibited, and the 25-day survival rate (SR) was only 17%. In the group inoculated with the blend, the survival rate increased to 50% due to the adjuvant effect of the microsphere, but the tumor grew fast in the early stage. In the group inoculated with the opening-sealed microcapsule loaded with OVA, the tumor was apparently suppressed in the early stage and grew slowly, and the 25-day survival rate was as high as 100%, indicating that even without a molecular adjuvant, the microcapsule system achieved better therapeutic effects through the full utilization of the antigen. As shown in the group inoculated with the opening-sealed microcapsule loaded with OVA and MPLA, a small amount of the adjuvant MPLA (3 µg) not only increased the survival rate to as high as 100%, but also significantly inhibited the growth of the tumor. On the 26th day, 50% of the mice had tumors the size of which was basically the same as that at the beginning of the treatment, and more than 60% of the mice survived more than 40 days. That proved that the compatibility between the microsphere system and MPLA further enhanced tumor suppression.

Example 8. Effect of Opening-Sealed Microcapsule on B16 Melanoma Solid Tumor in Animal To construct B16 tumor-bearing mice models, 5×10$^5$ B16 melanoma cells (provided by Jinlin University) were injected into 6-8 weeks old female C57BL/6 mice (purchased from Beijing Weitonglihua Experimental Animal Co., Ltd.) on the armpit, and the tumor-bearing mice were randomly divided into groups each consisting of 6 mice. The mice were vaccinated when the tumor grew to an area of greater than 10 mm$^2$ on the 4th day. The four groups of mice were vaccinated respectively as follows: a group was inoculated with PBS, a group was inoculated with high-dose (50 µg) MUC1 peptide a single time, a group was inoculated with the opening-sealed microcapsule loaded with MUC1 peptide (which comprised 3 mg of the microsphere and 50 µg of MUC1), and a group was inoculated with the opening-sealed microcapsule loaded with MUC1 and MPLA (which comprised 3 mg of the microsphere, 60 µg of MUC1, and 3 µg of MPLA). From the day the tumor models were constructed, the mice were observed for the hair, weight, and survival, and the length and width of the tumor were measured with a vernier caliper, every other day. The volume of the tumor was calculated by this formula: $V=1/2 \times L \times W^2$ (where L is the length of the tumor, and W is the width of the tumor).

Figure 16:
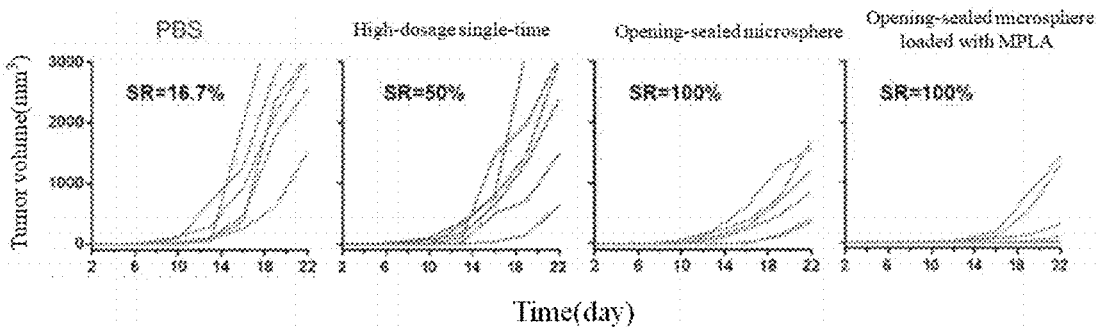
FIG. 16 shows tumor growth curves of B16 tumor-bearing mice with different vaccinations.

As shown in the tumor growth curve in FIG. 16, in the group inoculated with PBS and that inoculated with high-dose MUC1, the growth of melanoma was not effectively inhibited. In the group inoculated with the opening-sealed microcapsule loaded with MUC1 peptide, the growth of the tumor was significantly inhibited and 33% of the mice had tumors the size of which was smaller than 500 mm$^3$, and the survival rate within the 22 days of the monitoring was 100%. The group inoculated with the opening-sealed microcapsule loaded with MUC1 and MPLA exhibited the best antitumor effect, and in that group, on the 22th d ay, 50% of the mice had tumors that almost did not grow, and a few of the mice had melanoma even disappeared.

Example 9. Effect of Opening-Sealed Microcapsule on B16 Melanoma Metastasis in Animal To construct B16 tumor-bearing mice models, 2×10$^5$ B16 melanoma cells (provided by Jinlin University) were injected into 6-8 weeks old female C57BL/6 mice (purchased from Beijing Weitonglihua Experimental Animal Co., Ltd.) on the tail vein, and the tumor-bearing mice were randomly divided into groups each consisting of 6 mice. The mice were vaccinated on the 4th day. The four groups of mice were vaccinated respectively as in Example 8. On the 18th day after the inoculation, 2 mice in each group were killed for the observation of the metastasis of melanoma in the lungs and kidneys, and the number of the metastases in these organs was counted.

Figure 17A:
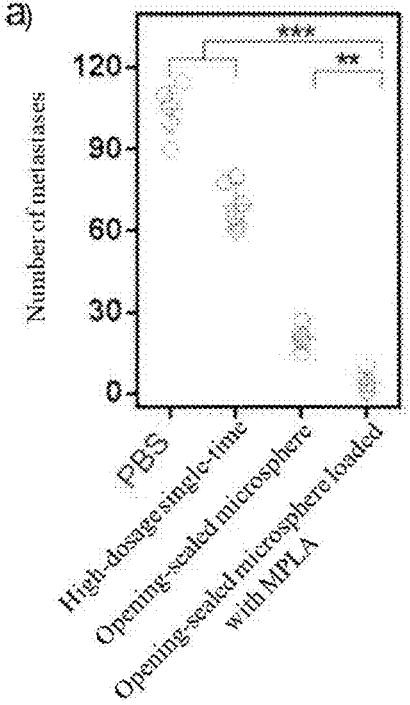
FIG. 17($a$) and FIG. 17($b$) shows a quantitative analysis of metastatic lesions in the lungs FIG. 17($a$) and the kidneys FIG. 17($b$) after different vaccinations.
Figure 17B:
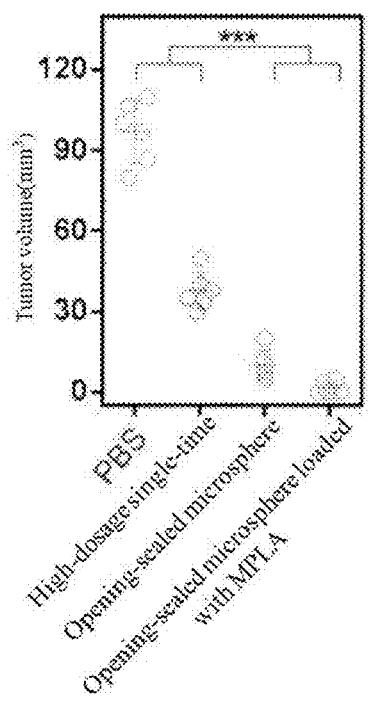

As shown in FIG. 17, in the group inoculated with PBS, a large number of melanoma metastases, about 100 per mice, appeared in the lungs, metastases in a total volume of 100 mm$^3$ grew in the kidneys, which confirmed the successful construction of melanoma metastasis models. 18 days after the vaccination, the mice in the group inoculated with the opening-sealed microcapsule loaded with MUC1 were dissected, and it was found that as compared with the PBS group, the number of melanoma metastases in the lungs decreased to 15-20 from 100, and the volume of the tumor in the kidneys decreased 10 mm$^3$ from 100 mm$^3$. As shown in the group inoculated with the opening-sealed microcapsule loaded with MUC1 and MPLA, the addition of MPLA further improved the anti-metastasis effect, and there are almost no obvious metastases in the lungs or in the kidneys. Therefore, the combination of the microcapsule system and the TLR receptor agonist produced the best anti-metastasis effect.

Example 10. Effect of Opening-Sealed Microcapsule Loaded with Tumor Neoantigen on 4T1 Breast Cancer in Animal The tumor neoantigen was a combination of 8 polypeptides in equal proportions (the amino acid sequences of which are SPNRSWVSL, HPMYLFLSM, VAVKVNFYVI, KAPHNFQFV, YHYVLNSMV, EYSAMTTRGTI, GSPPRFFYM, and CPQTHAVVL). The polypeptides were prepared as follows: The 4T1 tumor cell line and normal Balb/c mouse tissue (provided by the National Key Laboratory of Biochemical Engineering) were compared and sequenced to screen out the tumor mutant genes, and the computer algorithm was used to predict the mutant peptides (by Shenzhen Yuce Biotech Company), and then peptide synthesis was performed (by GenScript Biotechnology Company).

An AS04 adjuvant mixture for a group of mice described later was prepared as follows: MPLA was added to a 0.5% triethanolamine solution, heated to 65° C. and kept at that temperature for for 5 min to promote dissolution, and sonicated three times at the power of 60 W for 1 min. After MPLA dissolved completely, the pH of the solution was adjusted to around 7.4 with HCl. Subsequently, the MPLA aqueous solution was mixed with the aluminum adjuvant and sonicated for 30 s. To the mixture, was added the tumor neoantigen such that the vaccine comprised MPLA (3 μg), the aluminum adjuvant (100 μg) and the tumor neoantigen (200 μg) in 100 μL of normal saline.

The opening-sealed microcapsule loaded with the tumor neoantigen and MPLA was prepared as in Example 3.

To construct 4T1 tumor-bearing mice models, $5 \times 10^5$ B16 4T1 breast cancer cells (purchased from ATCC) were injected into 6-8 weeks old female C57BL/6 mice (purchased from Beijing Weitonglihua Experimental Animal Co., Ltd.) on the lower right mammary fat pad, and the tumor-bearing mice were randomly divided into groups each consisting of 6 mice. The mice were vaccinated on the 4th day.

The four groups of mice were vaccinated respectively as follows: a group was inoculated with PBS, a group was inoculated with the tumor neoantigen (200 μg), a group was inoculated with the AS04 adjuvant mixture (which comprised 100 μg of the aluminum adjuvant, 200 μg of the tumor neoantigen, and 3 μg of MPLA), and a group was inoculated with the opening-sealed microcapsule loaded with the tumor neoantigen and MPLA (which comprised 3 mg of the microsphere, 200 μg of the tumor neoantigen, and 3 μg of MPLA).

From the day the tumor models were constructed, the mice were observed for the hair, weight, and survival, and the length and width of the tumor were measured with a vernier caliper, every other day. The volume of the tumor was calculated by this formula: $V=1/2 \times L \times W^2$ (where L is the length of the tumor, and W is the width of the tumor).

Figure 18:
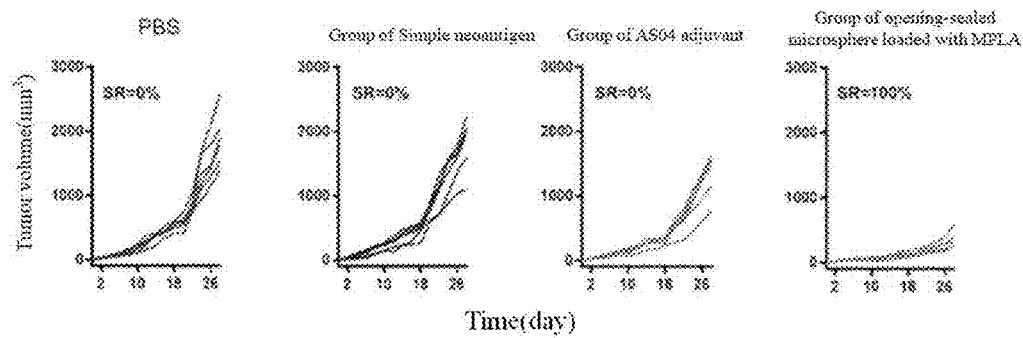
FIG. 18 shows tumor growth curves of 4T1 tumor-bearing mice with different vaccinations.

As shown by the tumor growth curves in FIG. 18, neither PBS nor the mere tumor neoantigen could effectively prevent breast cancer from growing, whereas the AS04 adjuvant mixture inhibited the growth of the tumor, evidenced by slow growth of the tumor. In comparison, the microcapsule group was the best in the antitumor effect: on the 28th day, 83% of the mice had tumors smaller than 500 mm³.

Example 11. Effect of Opening-Sealed Microcapsule Loaded with Tumor Neoantigen on 4T1 Breast Cancer Recurrence after Surgery in Animal To construct models of 4T1-luc breast cancer recurrence mice (purchased from Beijing Weitong Lihua Experimental Animal Co., Ltd.), $5 \times 10^5$ 4T1-luc breast cancer cells (purchased from ATCC) that have been transfected with luciferase were injected into 6-8 weeks old female Balb/c mice (purchased from Beijing Weitonglihua Experimental Animal Co., Ltd.) on the lower right mammary fat pad. After the tumors grew to 200 mm³, some of the tumors were surgically removed from the mice such that the remaining tumors were similar in size as observed by bioluminescence imaging. The mice were randomly divided into groups each consisting of 6 mice, and they were vaccinated on the second day.

The vaccination approach was the same as in Example 10. From the day the tumor models were constructed, the mice were observed for the hair, weight and survival every other day, the recurrence of the tumors were monitored by bioluminescence imaging, and the length and width of the tumor were measured with a vernier caliper and the volume of the tumor was calculated by this formula: $V=1/2 \times L \times W^2$ (where L is the length of the tumor, and W is the width of the tumor).

Figure 19:
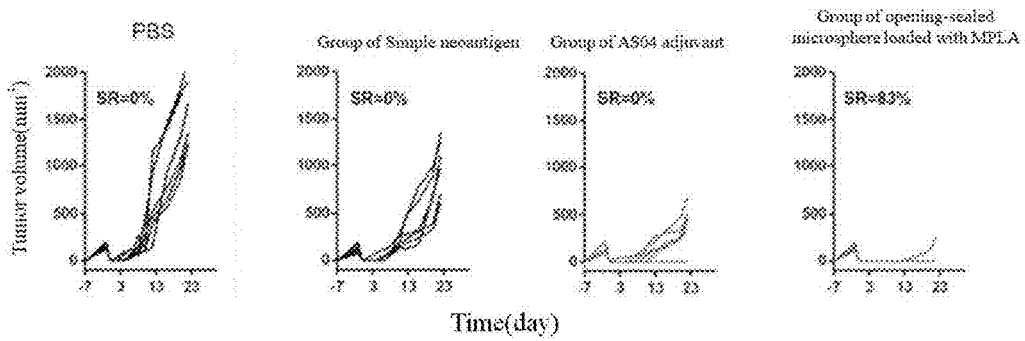
FIG. 19 shows growth curves of recurrent tumors after different vaccinations.
Figure 20:
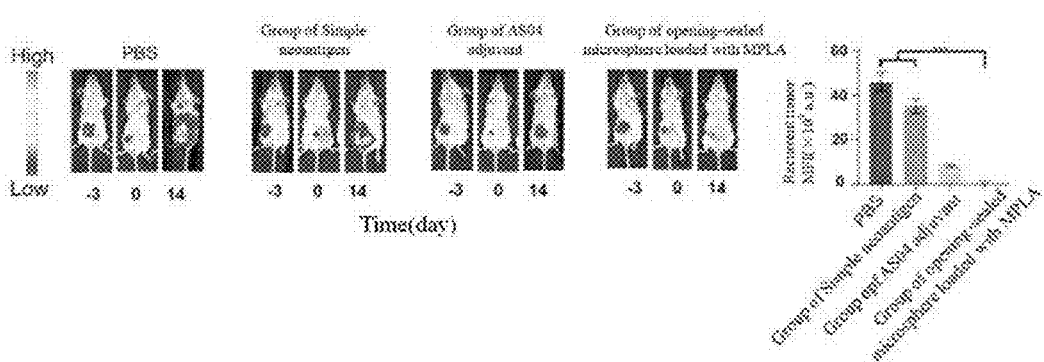
FIG. 20 shows bioluminescence imaging and a quantitative analysis of the postoperative recurrence model.

As shown by the tumor growth curves in FIG. 19, neither PBS nor the mere tumor neoantigen could effectively suppress the postoperative recurrence of breast cancer; all the mice developed tumor recurrence, and the tumor grew rapidly, lead to rapid death of the mice. The AS04 adjuvant mixture prevented tumor recurrence in some of the mice; although 13% of the mice had no visible tumor growth on the 22nd day, they died during the long-term monitoring. The microcapsule group was the best in postoperative reoccurrence resistance: on the 22nd day, only one mouse developed tumor recurrence, and 83% of the mice had no tumor recurrence. As shown by the pictures of bioluminescence imaging and the statistics in FIG. 22, after the resection, the volumes of the remaining tumor lesions were similar in size, but after being subjected to the different treatment strategies, the lesions exhibited apparently different levels of recurrence. In the opening-sealed microsphere group, no tumor lesions were found by bioluminescence imaging on the 14th day, whereas tumor recurrence occurred in all or part of the mice in the other groups.

Example 12. Effect of Opening-Sealed Microcapsule Loaded with Chemokine on Cell Recruitment 6-8 weeks old female C57BL/6 mice (n=4, purchased from Beijing Weitong Lihua Experimental Animal Co., Ltd.) were injected, on the back, with 3 mg of the blank opening-sealed microcapsules and 3 mg of opening-sealed microcapsules loaded with 7 μg of the chemokine GM-CSF. Five days later, the mice were killed. The portion of the mouse's back where the microcapsule was injected was opened, and the local subcutaneous tissue enclosing the carrier was taken out with tweezers. The tissue was cut with scissors, and it was soaked in 4% formalin solution for 24 hours. Then, the tissue was embedded with paraffin and subjected to sectioning, hematoxylin & eosin (H&E) staining and mounting. Finally, the slides were scanned using the Automated Quantitative Pathology Imaging System (Vectra 3.0, purchased from PerkinElmer) for the observation of the inflammatory response at the injection site.

Figure 21:
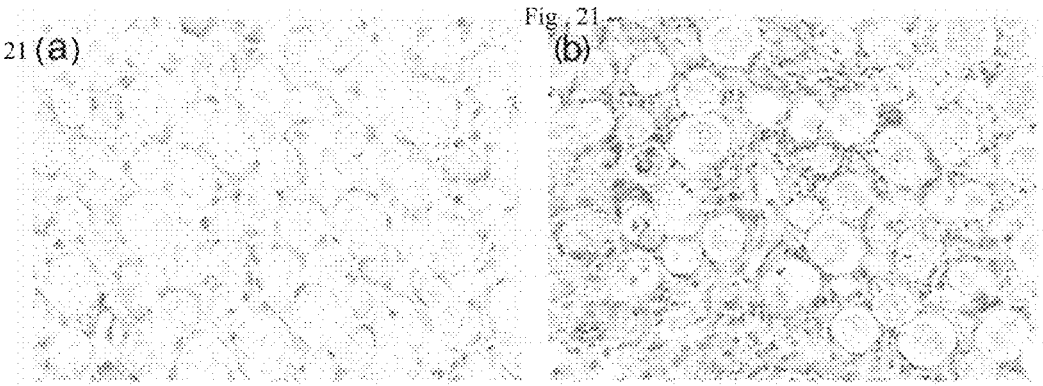
FIG. 21($a$) and FIG. 21($b$) shows H&E staining images of cell recruitment in the subcutaneous tissue by blank opening-sealed microcapsules FIG. 21($a$) and opening-sealed microcapsules loading with GM-CSF FIG. 21($b$).
Figure 21:
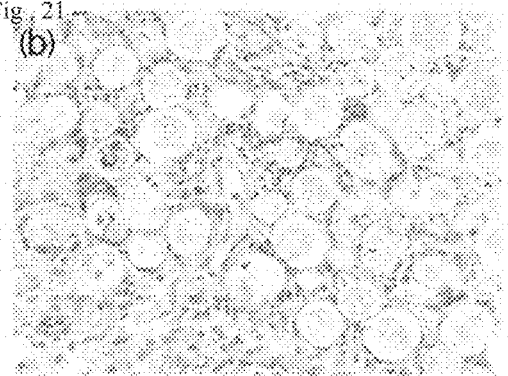

As shown in FIG. 21, after 5 days of metabolism in the body, only a small number of inflammatory cells (black dots) were recruited around the blank microspheres (light-colored rounds). The microcapsules loaded with GM-CSF recruited significantly more cells around them, which meant that the antigens released from the microcapsules loaded with GM-CSF were more phagocytized, thereby enhancing the efficiency of antigen presentation and the final immune effect.

What is claimed is:

1. A vaccine, comprising antigen and a matrix of biodegradable polymer blend, wherein the polymer blend comprises a lactide polymer and an amphiphilic block copolymer, and the vaccine exists in form of a microcapsule that comprises a multi-cavity structure inside, and has an average particle diameter of 10-100 μm, and wherein the microcapsule is prepared by making a porous microsphere from the polymer blend, then mixing the porous microsphere with an antigen-containing solution, and sealing openings of the porous microsphere that has been loaded with the antigen-containing solution to form an opening-sealed microcapsule loaded with the antigen, wherein the lactide polymer is polylactide and has a weight average molecular weight of 5,000-100,000 Daltons, the amphiphilic block copolymer is a copolymer of monomethoxy polyethylene glycol with polylactide and has a weight average molecular weight of 10,000-50,000 Daltons, the ratio by weight of the amphiphilic block copolymer to the matrix of the polymer blend in the microcapsule is at least 5%, the porous microsphere has a porosity of at least 40% or more, and has pores having a diameter of 800 nm-5 μm, the degradation of the polymeric matrix produces an acidic microenvironment that enhances antigen-presenting cells recruitment, and the vaccine is an antitumor vaccine.

2. The vaccine of claim 1, further comprising chemokine.

3. The vaccine of claim 1, further comprising an immunostimulatory enhancer.

4. The vaccine of claim 1, wherein the openings of the microsphere are sealed by heating the porous microsphere loaded with the antigen to a temperature proximate to the glass transition temperature of the microsphere.

5. The vaccine of claim 1, wherein the porous microsphere is prepared through a double-emulsion-solvent-removal method.

6. A pharmaceutical composition, comprising the vaccine or opening-sealed microcapsule according to claim 1, and a pharmaceutically acceptable carrier.

7. Use of the vaccine, porous microsphere, or opening-sealed microcapsule according to claim 1 in the preparation of an antitumor vaccine.

8. Use of the vaccine or opening-sealed microcapsule according to claim 1 in the preparation of an antitumor medicament, or a medicament for inducing a cytotoxic cell response to tumor cells or tumors.

9. The vaccine of claim 1, wherein the antigen is tumor antigen.

10. The vaccine of claim 2, wherein the chemokine comprises at least one of granulocyte-macrophage colony-stimulating factor (GM-CSF), macrophage inflammatory protein-3α (MIP-3α), and monocyte chemotactic protein-1 (MCP-1).

11. The vaccine of claim 3, the immunostimulatory enhancer is monophosphoryl lipid A, cytosine-guanine oligodeoxynucleotide, and/or polyinosinic acid.

12. The vaccine of claim 3, wherein the openings of the microsphere are sealed by heating the porous microsphere loaded with the antigen to a temperature 1-2° C. lower than the glass transition temperature of the microsphere.

* * * * *